(12) United States Patent
Maeda et al.

(10) Patent No.: US 7,585,981 B2
(45) Date of Patent: Sep. 8, 2009

(54) METHOD FOR PRODUCING TRIMER OF INDOLE DERIVATIVE, AND TRIMER OF INDOLE DERIVATIVE AND LAMINATED STRUCTURE THEREOF

(75) Inventors: Shinichi Maeda, Yokohama (JP); Fumino Momose, Otake (JP); Yoshikazu Saitoh, Yokohama (JP); Takashi Saitoh, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 316 days.

(21) Appl. No.: 11/437,581

(22) Filed: May 22, 2006

(65) Prior Publication Data

US 2006/0211793 A1 Sep. 21, 2006

Related U.S. Application Data

(62) Division of application No. 10/399,449, filed as application No. PCT/JP01/08442 on Sep. 27, 2001, now Pat. No. 7,115,751.

(30) Foreign Application Priority Data

Oct. 17, 2000 (JP) ............................ 2000-317045
May 28, 2001 (JP) ............................ 2001-159604

(51) Int. Cl.
*C07D 209/56* (2006.01)
(52) U.S. Cl. ...................................... 548/416; 548/455
(58) Field of Classification Search ...................... None
See application file for complete search history.

(56) References Cited

U.S. PATENT DOCUMENTS 5,290,891 A   3/1994   Billaud et al.

OTHER PUBLICATIONS

Paola Manini et al.: "Acid-promoted competing pathways in the oxidative polymerization of 5,6-dihydroxyindoles and related compounds: straight forward cyclo-trimerization routes to diindolocarbazole derivatives" J.Org.Chem., vol. 63, pp. 7002-7008 1998.

Peter Jennings et al.: "Electrooxidation of 5-substituted indoles" J. Chem. Soc., Faraday Trans., vol. 93, No. 21 pp. 3791-3797 1997.

Luceido Greci et al.: "Oxidative trimerization of indole: on the formation of dictations and radical cations by reaction of indole and nitrosobenzene in the presence of acids" J. Chem. Soc., Perkins Trans. 2, No. 11, pp. 2337-2342.

G. Kokkindis et al.: "Electrochemical behaviour of nitroindoles: oxidation electropolymerization and reduction of the nitro group of polymerized and non-polymerized 4-nitro and 5-nitroindole" Journal of Electroanalytical Chemistry, vol. 414, pp. 197-208, 1996.

Takao Kaneko et al.: "A novel indole trimer; diindolo [2,3-a: 2',3'-c]carbazole" Heterocycles, vol. 12, No. 4, pp. 471-473 1979.

Takao Kaneko et al.: "Reactions of indole with hydroxyl radicals and X-ray crystal structure of a novel indole trimer, 14-acetyldiindolo[2,3-a: 2',3'-c]carbazole" Chem. Pharm. Bull., vol. 29, No. 12, pp. 3499-3506 1981.

Vittorio Bocchi et al.: "The synthesis and structural characterization of a charge transfer complex of iodine and indole Trimer" Synthetic Metals, vol. 80, pp. 309-313 1996.

*Primary Examiner*—Kamal A Saeed
(74) *Attorney, Agent, or Firm*—Oblon, Spivak, McClelland, Maier & Neustadt, P.C.

(57) ABSTRACT

The present invention provides an industrial method that allows to produce an indole derivative trimer with high purity in mass, as well as novel indole derivative trimers obtainable by the method, having high conductivity, high oxidation-reduction potential, high oxidation-reduction capacity, and the excellent cycle characteristics. The present invention relates to a method of producing an indole derivative trimer comprising the step of oxidizing an indole derivative in a reaction solution containing an organic solvent and to the novel trimers produced by the method.

36 Claims, 6 Drawing Sheets

METHOD FOR PRODUCING TRIMER OF INDOLE DERIVATIVE, AND TRIMER OF INDOLE DERIVATIVE AND LAMINATED STRUCTURE THEREOF

CROSS REFERENCES TO RELATED APPLICATIONS

This application is a divisional application of U.S. patent application Ser. No. 10/399,449, now allowed, and claims priority to Unites States patent application Ser. No. 10/399,449.

FIELD OF THE INVENTION

The present invention relates to a method of producing indole derivative trimers as well as to novel indole derivative trimers obtainable by the method. The compositions containing any of the trimers as a main ingredient are applicable for various types of prevention of electrification, electrostatic shielding, capacitors, cells, EMI shielding agents, chemical sensors, display elements, organic EL materials, non-linear materials, antirust agents, adhesives, textiles, antistatic paints, electrodeposition painting, plating primers, conductive primers for electroostatic coating, electrolytic protection.

BACKGROUND TECHNOLOGY

As a method of chemically polymerizing indole, JP-A-5-148320 proposes a method including the step of dripping an indole solution into an oxidant solution. This method assumes only the case where indole containing no substituent is used as the raw material. There is no mention of an indole derivative containing a substituent. In addition, the product is a polymer containing indole as a repeating unit, and the publication does not include any description concerning formation of trimer.

Synthesis of polymer by means of an electrolytic reaction of indole without any substituent, 4-nitroindole or 5-nitroindole is described in J. Electroanal. Chem., 414 (1996), p. 197 and synthesis of a trimer by means of an electrolytic reaction of indole without any substituent or 5-cyanindole is described in J. Chem. Soc., Faraday Trans., 93 (1997), p. 3791, respectively. When an oxidation and reduction testing (cycle testing) is performed using the unsubstituted or substituted indole produced by the method described in the documents, degradation of the trimer occurs, and as a result the cycle characteristics is rather poor, and the products can hardly be applied for production of conductive devices. Further, it is impossible to synthesize trimers on a large scale by the electrolytic reaction, and the method can hardly be employed as an industrial process.

Synthesis of unsubstituted trimer using $TiCl_3$ or $FeSo_4$ and $H_2O_2$ is reported in Heterocycles, 12 (1979), p. 471, and in Chem. Pharm. Bull., 29, (1981), p. 3499. As described in the articles, however, there are many disadvantages, for instance, that several types of byproducts are mixed in the product, and that the yield of the target trimer is rather low.

Further, synthesis of unsubstituted indole trimer by means of the electrolytic reaction is disclosed also in Synthetic Metals, 80 (1996), p. 309. The physical properties of the trimer are: the interlaminar spacing of 0.658 nm and conductivity of 0.03 S/cm.

As described above, the unsubstituted and substituted indole trimers produced by the conventional technology have the insufficient cycle characteristics and low adaptability to industrial production. Therefore, the development of indole derivative trimers having a high oxidation-reduction potential, a high oxidation-reduction capacity, and excellent cycle characteristics, as well as the development of a method of industrially producing the indole derivative trimers have been very important problems to be solved in the art.

It is an object of the present invention to provide a method capable of industrially producing indole derivative trimers with high purity as well as to provide novel indole derivative trimers having a high conductivity, a high oxidation-reduction potential, a high oxidation-reduction capacity, and excellent cycle characteristics, obtainable by the method.

DISCLOSURE OF THE INVENTION

A first aspect of the present invention relates to a method of producing indole derivative trimer of the following formula (2):

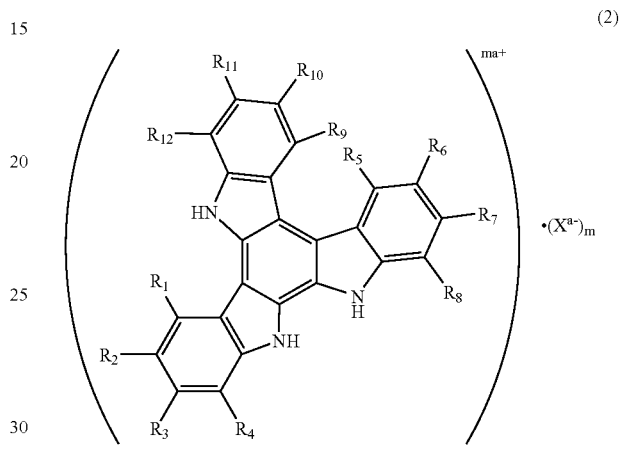

(2)

wherein $R_1$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5, comprising:

reacting at least one type of indole derivative of the following formula (1):

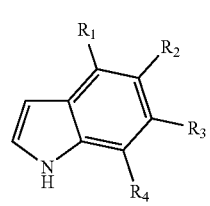

(1)

wherein $R_1$ to $R_4$ are substituents selected independently from the group consisting of hydrogen, linear or branched alkyl group having 1 to 24 carbon atoms, linear or branched alkoxy group having 1 to 24 carbon atoms, linear or branched acyl group having 2 to 24 atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group, in a reaction mixture containing at least one oxidant (B) and at least one organic solvent (C).

A second aspect of the present invention relates to a method of producing the indole derivative trimer of formula (2) above, comprising:

dripping a solution containing at least one type of oxidant (B), at least one type of organic solvent (C) and water into a solution containing at least one type of indole derivative (A) of formula (1) and at least one type of organic solvent (C).

A third aspect of the present invention relates to the method of producing an indole derivative trimer according to the first or second aspect of the present invention as described above, wherein the oxidant (B) is at least one type of oxidant selected from the group consisting of ferric chloride anhydrate, ferric chloride hexahydrate, ferric nitrate hexahydrate, ferric sulfate n-hydrate, ferric sulfate ammonium dodecahydrate, ferric perchlorate n-hydrate, cupric chloride, cupric tetrafluoroborate, ozone, and ammonium persulfate.

A fourth aspect of the present invention relates to the method of producing an indole derivative trimer according to any of the first to third aspects of the present invention, wherein the organic solvent (C) is acetonitrile.

A fifth aspect of the present invention relates to the method of producing an indole derivative trimer according to any of the first to fourth aspects of the present invention, further comprising:

performing a doping treatment with an acidic solution after the end of the reaction.

A sixth aspect of the present invention relates to an indole derivative trimer of following formula (3):

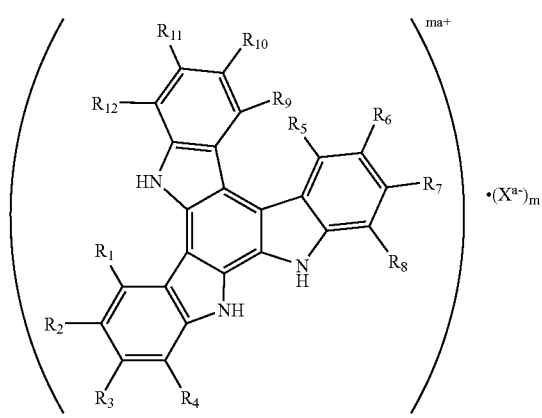

(3)

wherein $R_1$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, a linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group, providing that the cases where all of $R_1$ to $R_{12}$ are hydrogen and where all of $R_2$, $R_6$ and $R_{10}$ are the same and the rest of the substituents are all hydrogen are excluded;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A seventh aspect of the present invention relates to a 4-nitroindole trimer derivative of the following formula (4):

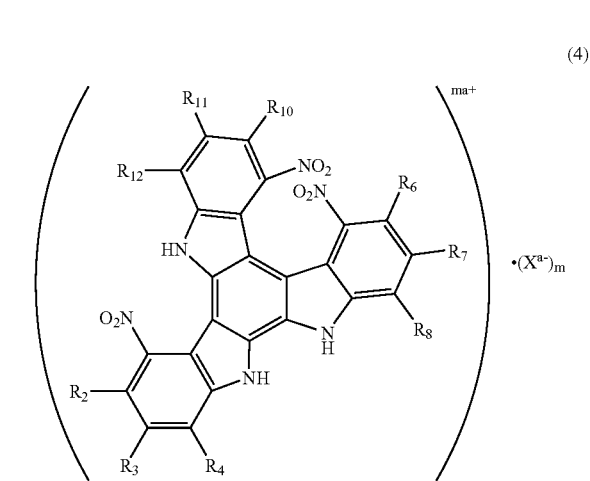

(4)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

An eighth aspect of the present invention relates to a 6-nitroindole trimer derivative of following formula (5):

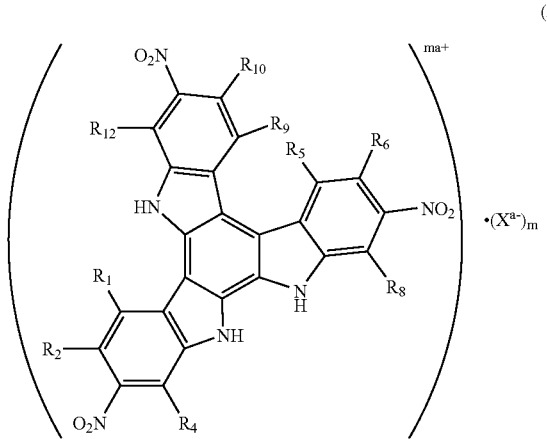

wherein $R_1$, $R_2$, $R_4$ to $R_6$, $R_8$ to $R_{10}$ and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A ninth aspect of the present invention relates to a 7-nitroindole trimer derivative of the following formula (6):

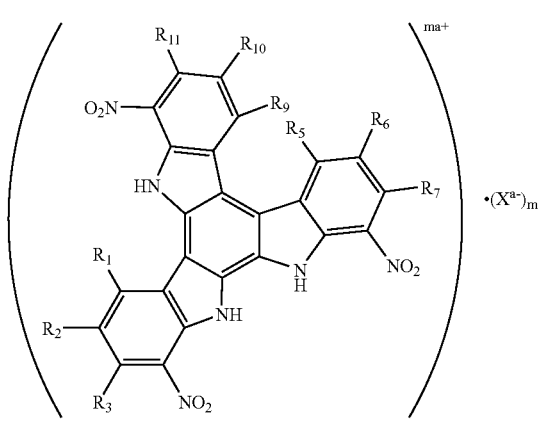

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A tenth aspect of the present invention relates to an indole-4-carbonitrile trimer derivative expressed by the following formula (7):

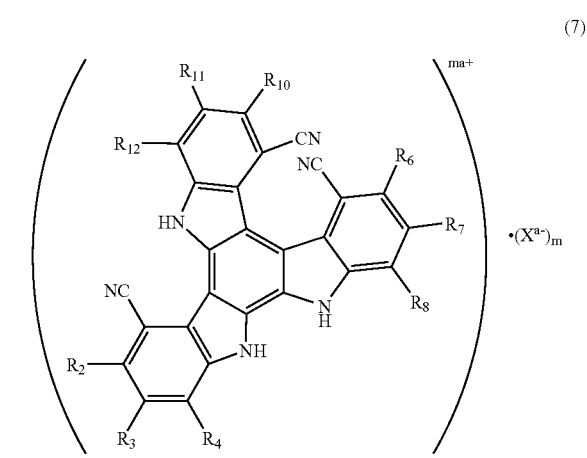

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

An 11-th aspect of the present invention relates to an indole-6-carbonitrile trimer derivative of the following formula (8):

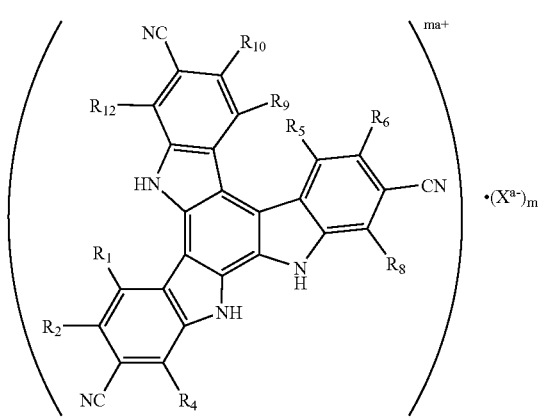

(8)

wherein $R_1$, $R_2$, $R_4$ to $R_6$, $R_8$ to $R_{10}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 12-th aspect of the present invention relates to an indole-7-carbonitrile trimer derivative of the following formula (9):

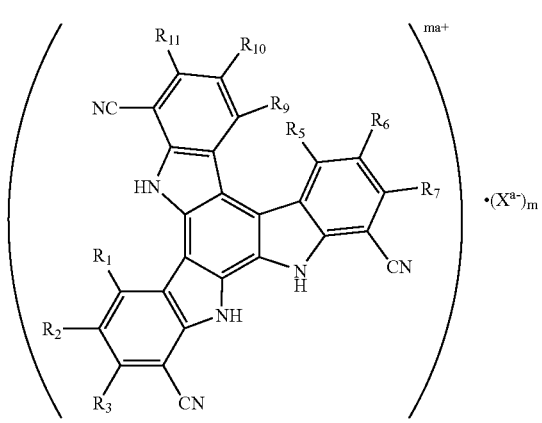

(9)

wherein $R_1$ to $R_3$, $R_5$ to $R_7$, and $R_9$ to $R_{11}$, are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 13-th aspect of the present invention relates to an indole-4-carboxylic acid trimer derivate of formula (10):

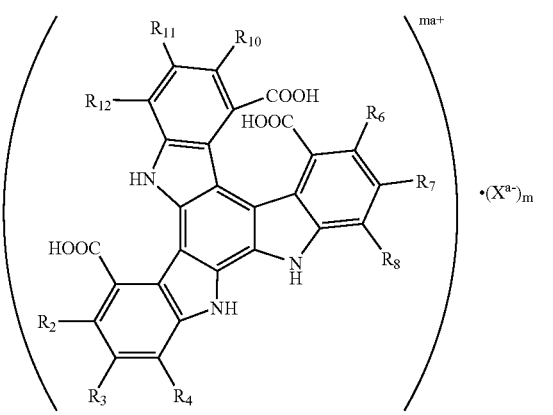

(10)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 14-th aspect of the present invention relates to an indole-6-carboxylic acid trimer derivative of following formula (11):

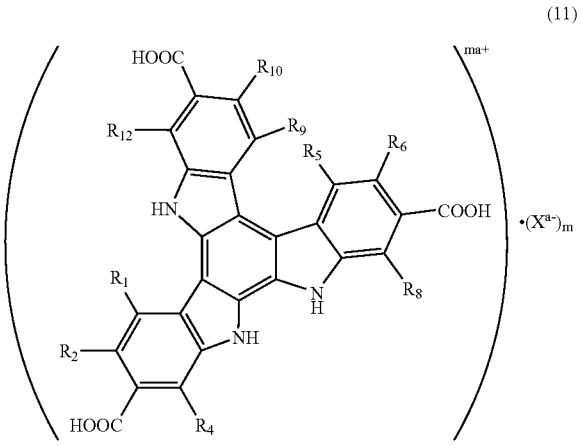

wherein $R_1$, $R_2$, $R_4$ to $R_6$, $R_8$ to $R_{10}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 15-th aspect of the present invention relates to an indole-7-carboxylic acid trimer derivative of formula (12):

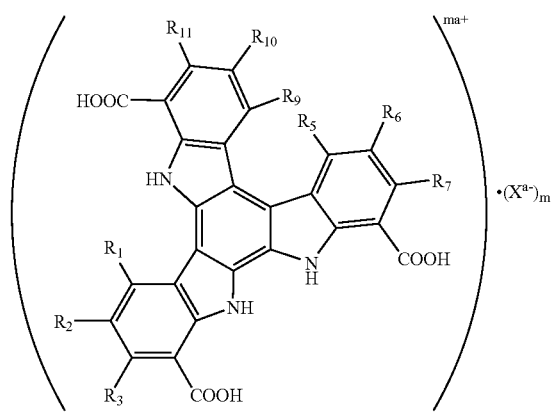

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 16-th aspect of the present invention relates to an indole-4-carbaldehyde trimer derivate of following formula (13):

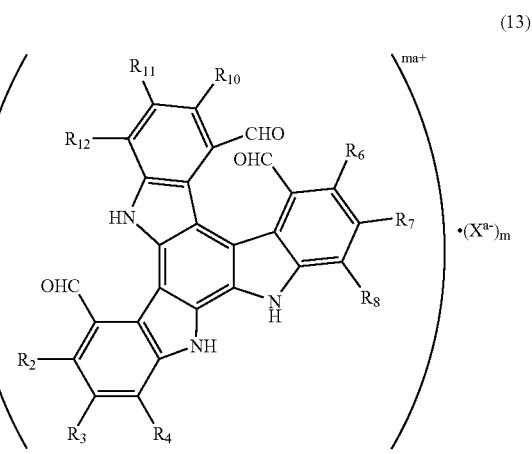

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 17-th aspect of the present invention relates to an indole-5-carbaldehyde trimer derivative of following formula (14),

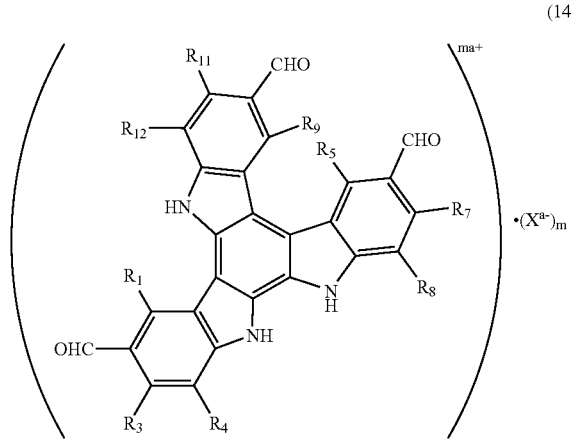

(14)

wherein $R_1$, $R_3$ to $R_5$, $R_7$ to $R_9$, $R_{11}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

An 18-th aspect of the present invention relates to an indole-6-carbaldehyde trimer derivative of formula (15):

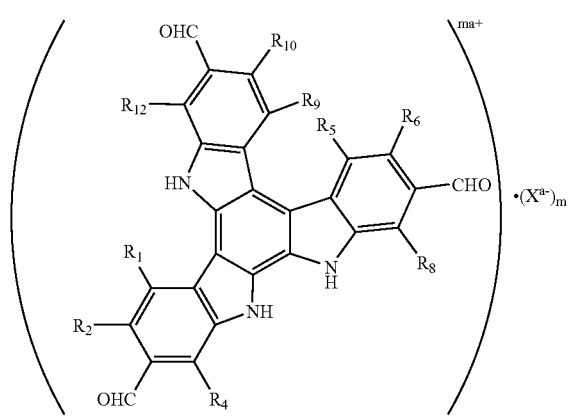

(15)

wherein $R_1$, $R_2$, $R_4$ to $R_6$, $R_8$ to $R_{10}$ and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 19-th aspect of the present invention relates to an indole-7-carbaldehyde trimer derivative of following formula (16):

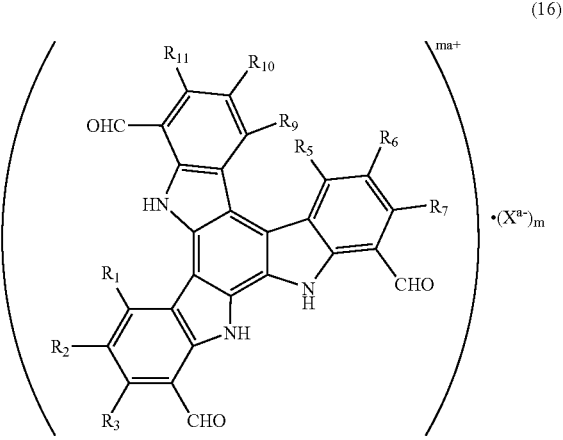

(16)

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 20-th aspect of the present invention relates to 4-bromoindole trimer derivative expressed by following formula (17):

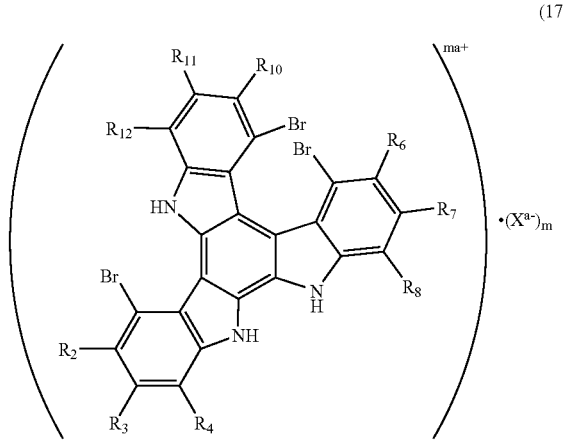

(17)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 21-st aspect of the present invention relates to a 6-bromoindole trimer derivative of following formula (18):

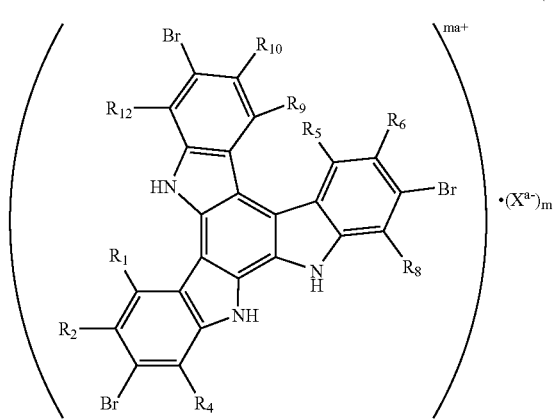

(18)

wherein $R_1$, $R_2$, $R_4$ to $R_6$, $R_8$ to $R_{10}$ and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 22-nd aspect of the aspect of the present invention relates to a 7-bromoindole trimer derivative of following formula (19):

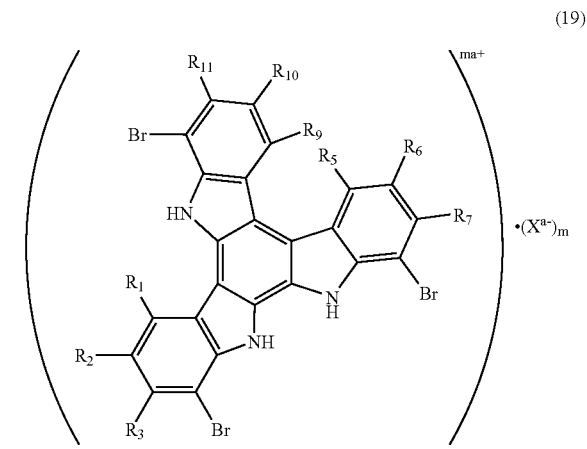

(19)

wherein all of $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 23-rd aspect of the present invention relates to a 4-fluoroindole trimer derivative of following formula (20):

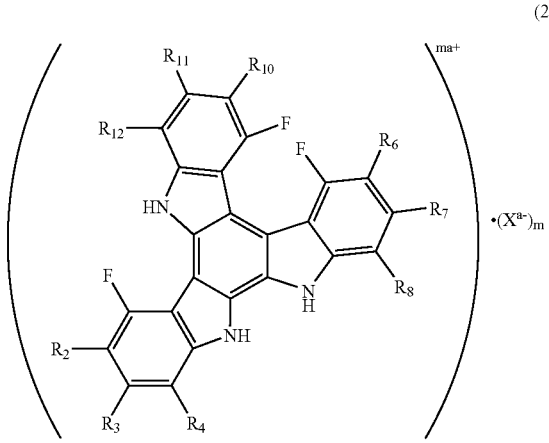

(20)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 24-th aspect of the present invention relates to a 5-fluoroindole trimer derivative of following formula (21):

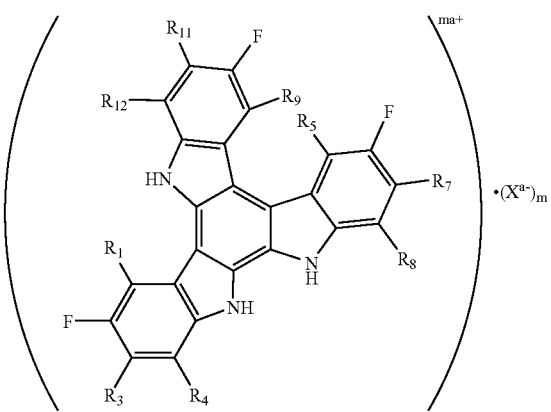

(21)

wherein $R_1$, $R_3$ to $R_5$, $R_7$ to $R_9$, $R_{11}$ and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 25-th aspect of the present invention relates to a 6-fluoroindole trimer derivative of following formula (22):

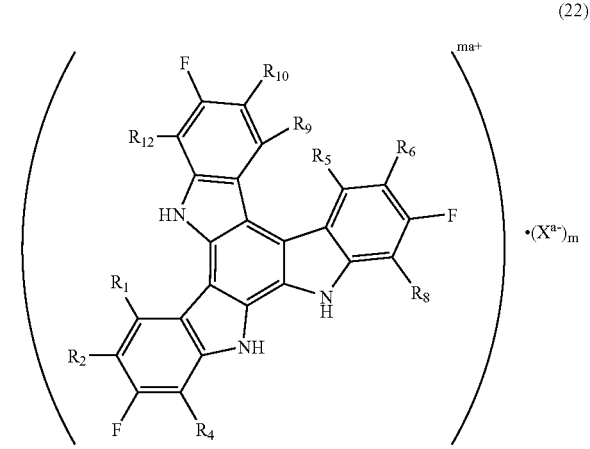

(22)

wherein $R_1$, $R_2$, $R_4$ to $R_6$, $R_8$ to $R_{10}$ and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 26-th aspect of the present invention relates to a 7-fluoroindole trimer derivative of following formula (23):

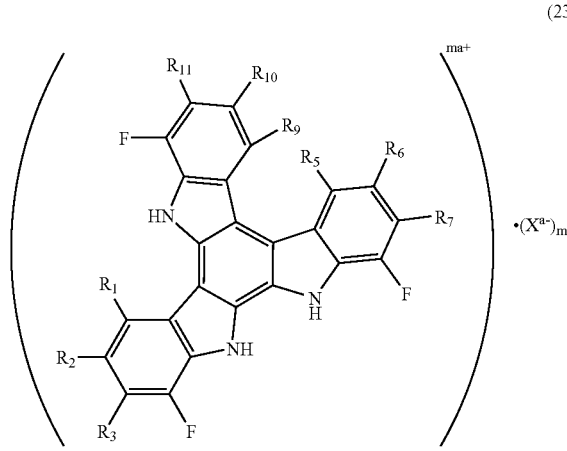

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 27-th aspect of the present invention relates to a 4-acetylindole trimer derivative of following formula (24):

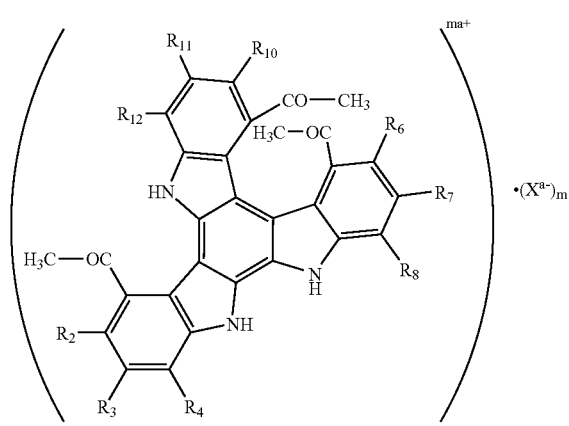

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 28-th embodiment of the present invention relates to a 5-acetylindole trimer derivative of following formula (25):

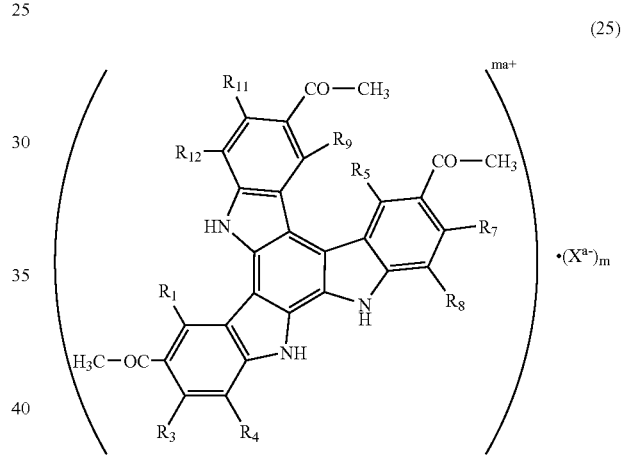

wherein $R_1$, $R_3$ to $R_5$, $R_7$ to $R_9$, $R_{11}$ and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 29-th aspect of the present invention relates to a 6-acetyl-indole trimer derivative of following formula (26):

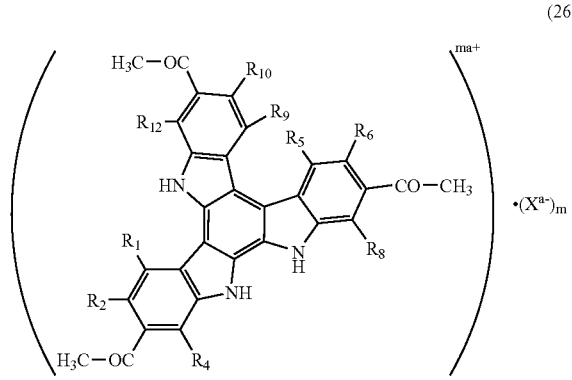

(26)

wherein $R_1$, $R_2$, $R_4$ to $R_6$, $R_8$ to $R_{10}$ and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ions nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 30-th aspect of the present invention relates to a 7-acetyl-indole trimer derivative of following formula (27):

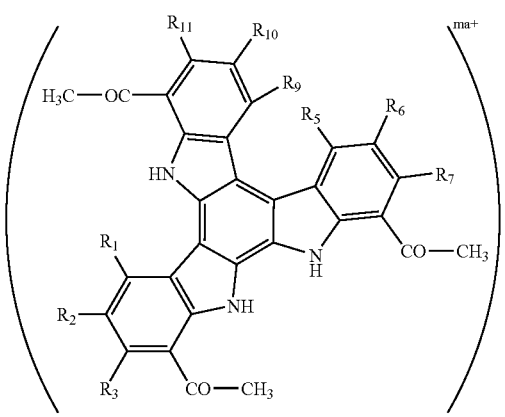

(27)

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 31-st aspect of the present invention relates to a 4-carbamoylindole trimer derivative of following formula (28):

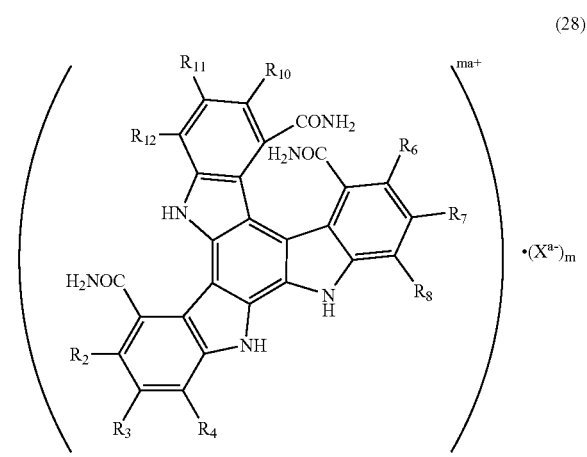

(28)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 32-nd aspect of the present invention relates to a 5-carbamoylindole trimer derivative of following formula (29):

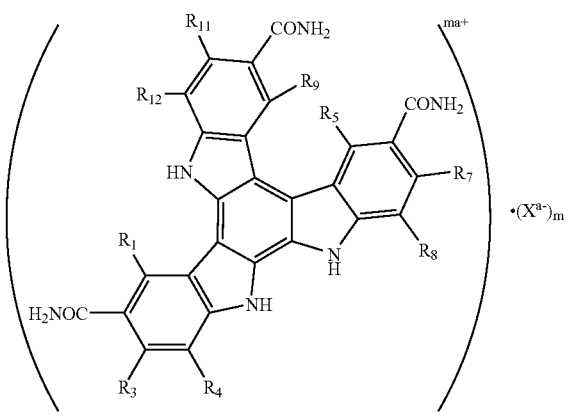

(29)

wherein $R_1$, $R_3$ to $R_5$, $R_7$ to $R_9$, $R_{11}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 33-rd aspect of the present invention relates to a 6-carbamoylindole trimer derivative of following formula (30):

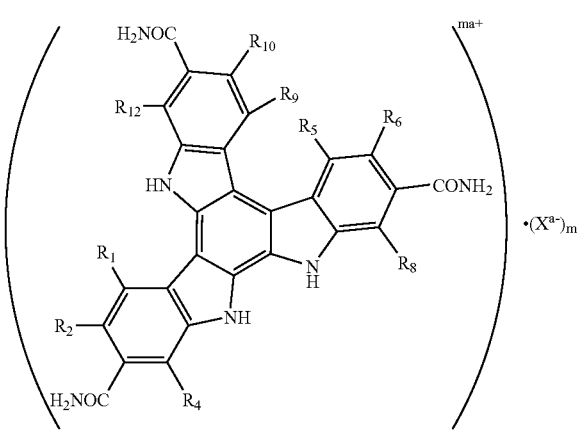

(30)

wherein $R_1$, $R_2$, $R_4$ to $R_6$, $R_8$ to $R_{10}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 34-th aspect of the invention relates to a 7-carbamoylindole trimer derivative of formula (31):

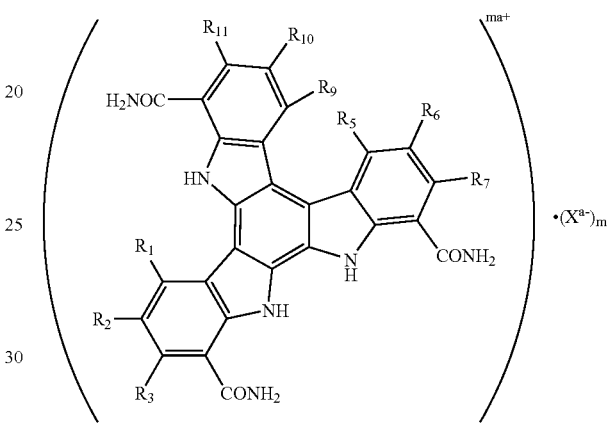

(31)

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

A 35-th aspect of the present invention relates to the indole derivative trimer according to any of the aspects 6 through 34, wherein $X^{a-}$ is at least one member selected from the group consisting of chlorine ion, sulfate ion, and fluoroborate ion.

A 36-th aspect of the present invention relates to the indole derivative trimer according to any of the aspects 6 through 35, wherein the indole derivative trimer is of doped type with m=0.001-0.5.

A 37-th aspect of the present invention relates to the indole derivative trimer according to any of the aspects 6 to 35, wherein the indole derivative trimer is of undoped type m=0.

A 38-th aspect of the present invention relates to an indole derivative trimer of following formula (2) in the form of particles having a particle diameter of 0.1 to 50 μm:

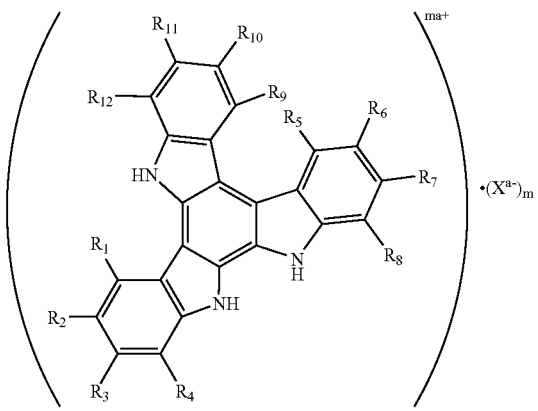

(2)

wherein $R_1$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0 to 0.5.

An 39-th aspect of the present invention relates to the indole derivative trimer according to claim 38, wherein the indole derivative trimer is obtainable by the method according to any of the aspects 1 to 5.

A 40-th aspect of the present invention relates to the indole derivative trimer according to the aspect 38, wherein the indole derivative trimer is the indole derivative trimer of any one of claims 6 to 37.

A 41-st aspect of the present invention relates to the indole derivative trimer according to the aspect 38 or 39, wherein the indole derivative trimer is indole-5-carbonitrile trimer or an indole-5-carboxylic acid trimer of following formula (32):

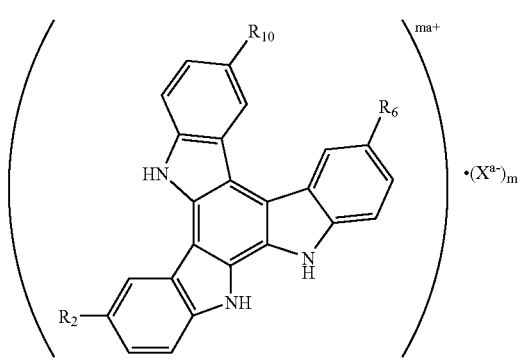

(32)

wherein $R_2$, $R_6$, and $R_{10}$ are substituted by cyano group or carboxyl group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and a trifluoromethane sulfonate ion;

a is an integral number in the range from 1 to 3 indicating the ionic valence of the ion X; and m is a number in the range from 0 to 0.5.

A 42-nd aspect of the present invention relates to a laminated structure of indole derivative trimer of following formula (2), having an interlaminar spacing of 0.1-0.6 nm:

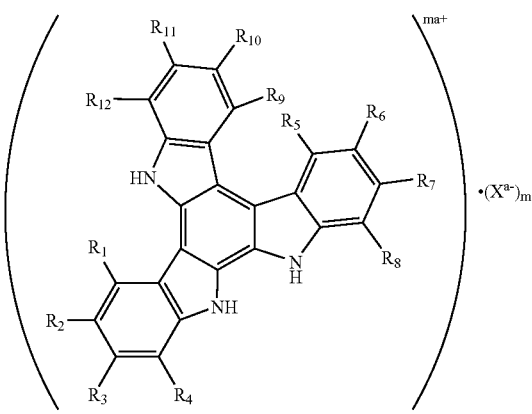

(2)

wherein $R_1$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 indicating the ionic valence of the ion X; and m is a number in the range from 0 to 0.5.

A 43-rd aspect of the present invention relates to the laminated structure of indole derivative trimer according to the aspect 42, wherein the indole derivative trimer is obtainable by the method according to any of the aspects 1 to 5.

A 44-th aspect of the present invention relates to the laminated structure of indole derivative trimer according to the aspect 42, wherein the indole derivative trimer is the indole derivative trimer of any of the aspects 6 to 37.

A 45-th aspect of the present invention relates to the laminated structure of the indole derivate trimer according to the aspects 42 or 43, wherein the indole derivative trimer is indole-5-carbonitrile trimer or indole-5-carboxylic acid trimer of following formula (32):

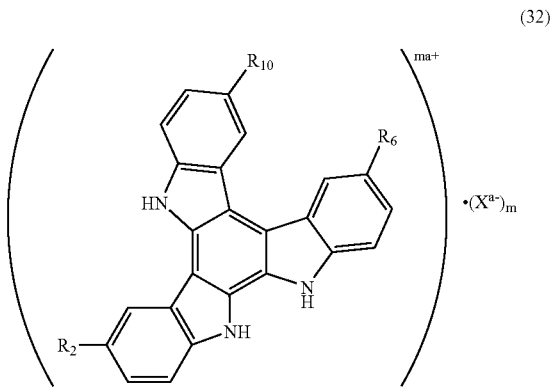

(32)

wherein $R_2$, $R_6$, and $R_{10}$ are substituted by cyano group or carboxyl group;

$X^{a-}$ is at least one anion selected from the group of monovalent to tervalent anions group consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 indicating the ionic valence of the ion X; and m is a number in the range from 0 to 0.5.

BEST MODE FOR CARRYING OUT THE INVENTION

Figure 1:
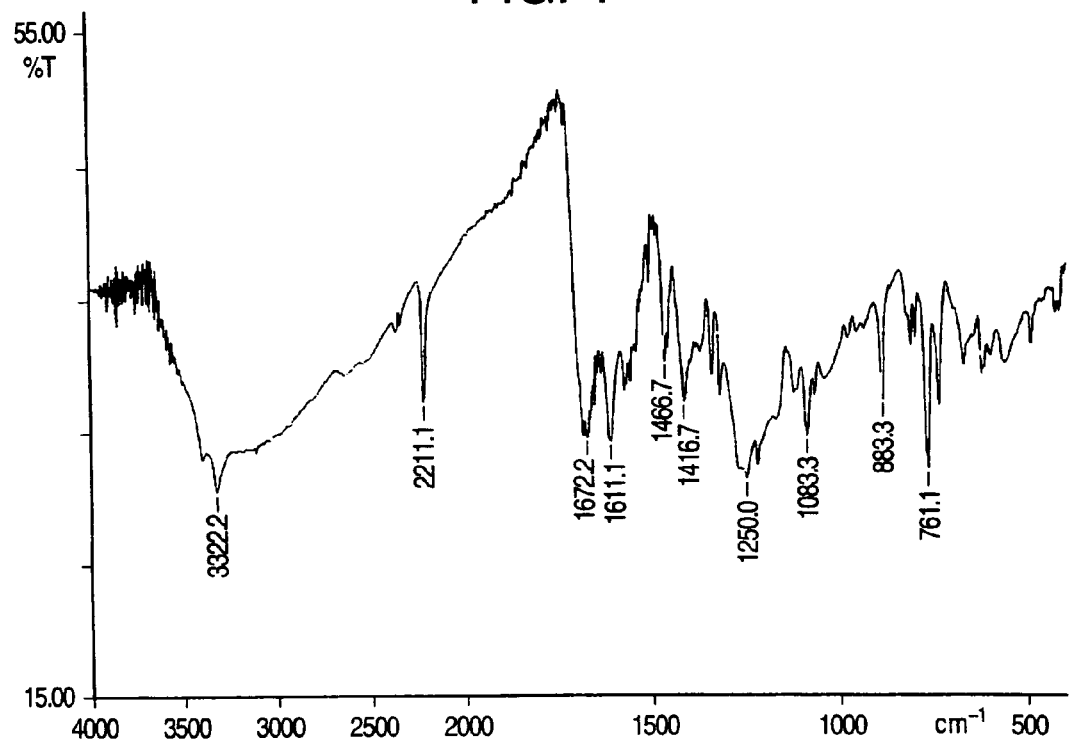
FIG. 1 is an IR chart showing indole-6-carbonitrile trimer according to Example 1.
Figure 2:
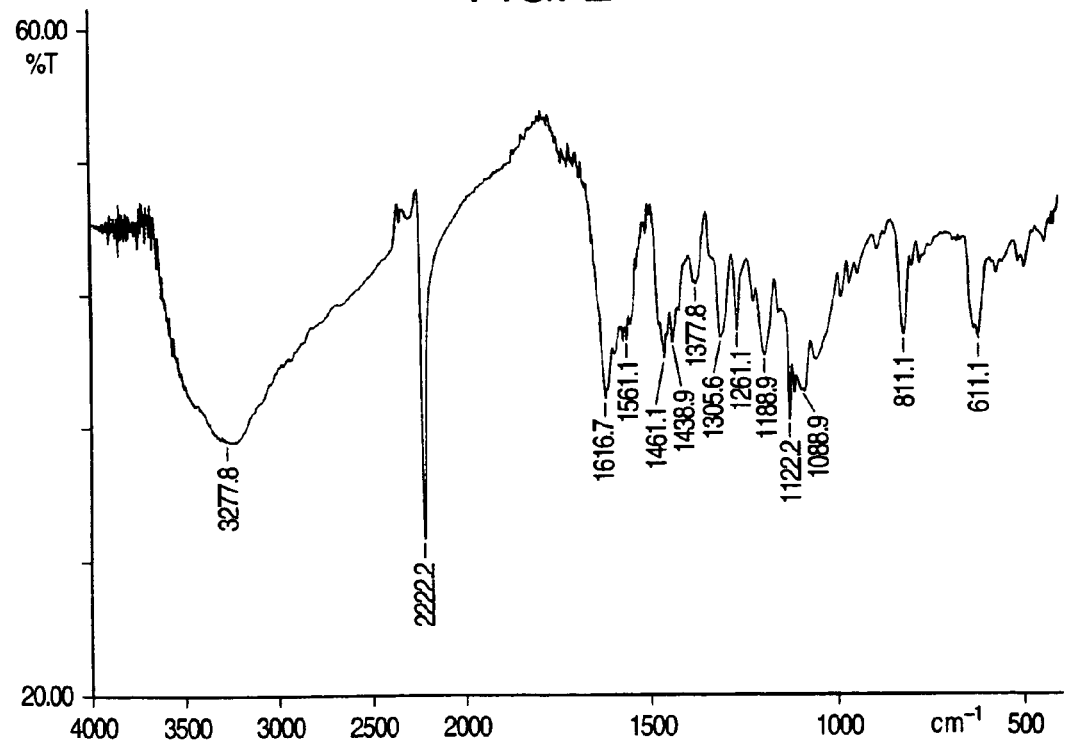
FIG. 2 is an IR chart showing indole-5-carbonitrile trimer according to Example 2.
Figure 3:
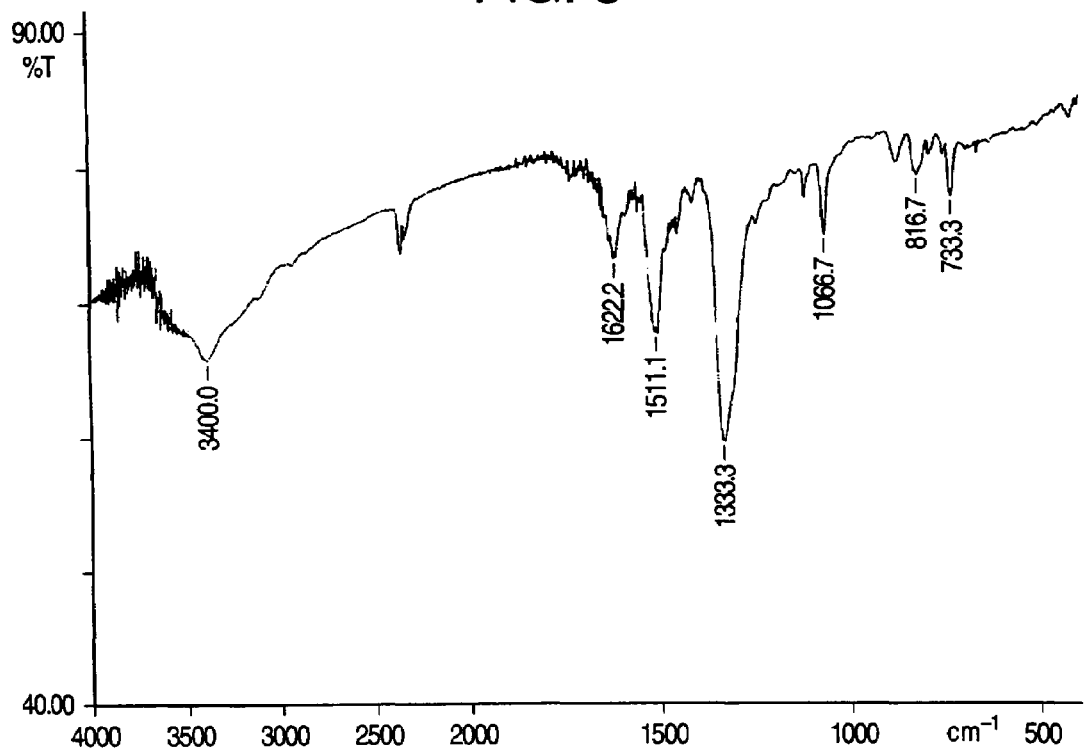
FIG. 3 is an IR chart showing 6-nitroindole trimer according to Example 3.
Figure 4:
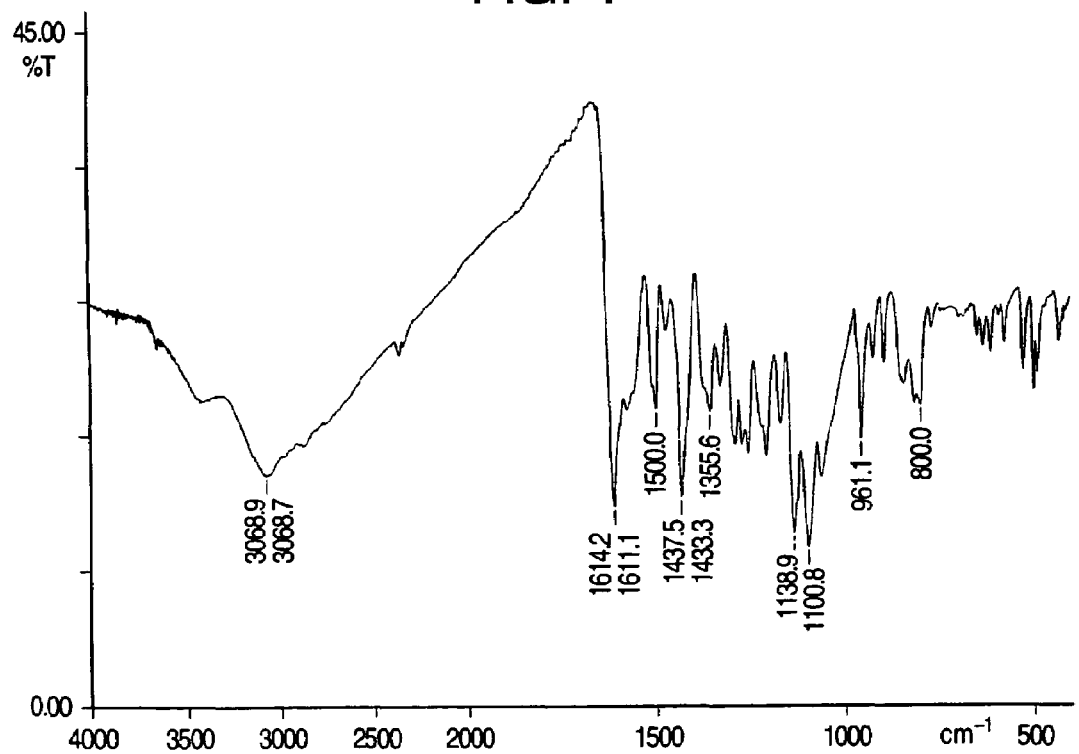
FIG. 4 is an IR chart showing 6-fluoroindole trimer according to Example 4.
Figure 5:
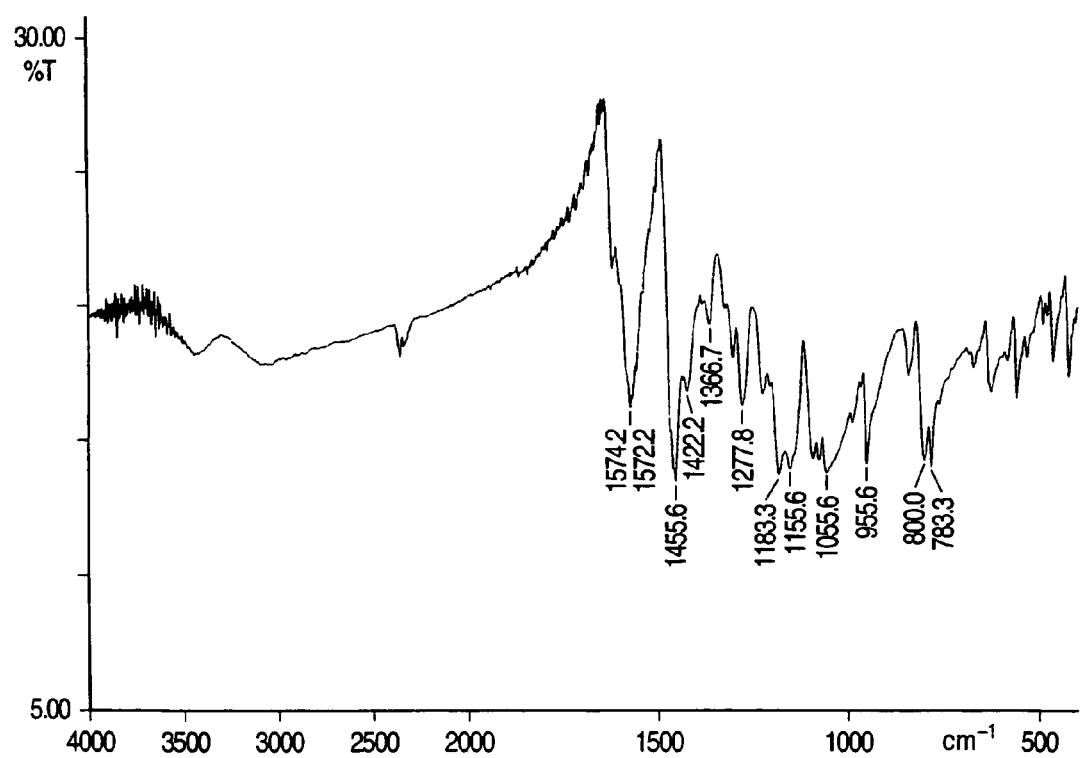
FIG. 5 is an IR chart showing 5-fluoroindole trimer according to Example 6.
Figure 6:
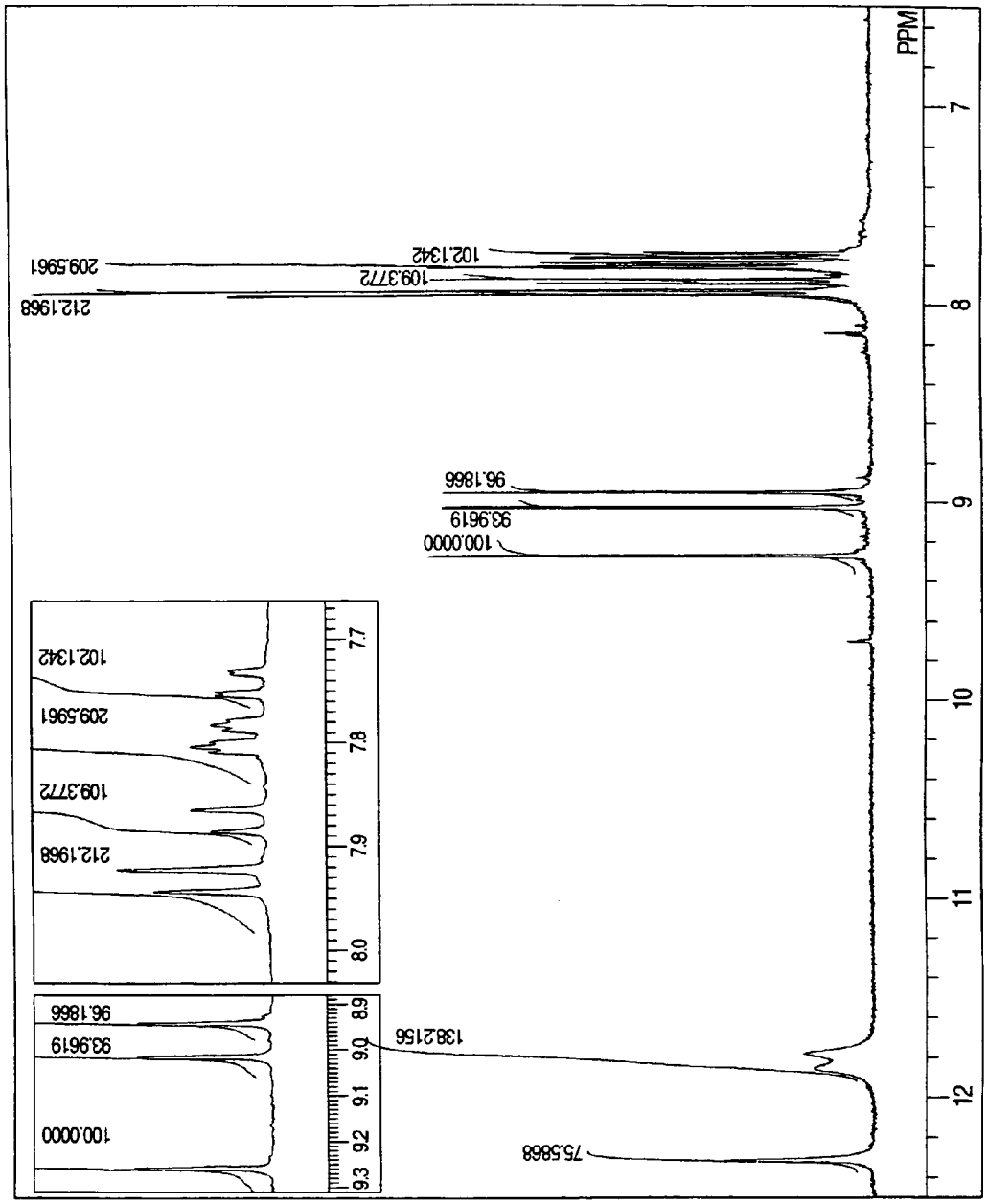
FIG. 6 is an NMR chart showing indole-5-carbonitrile trimer according to Example 2.
Figure 7:
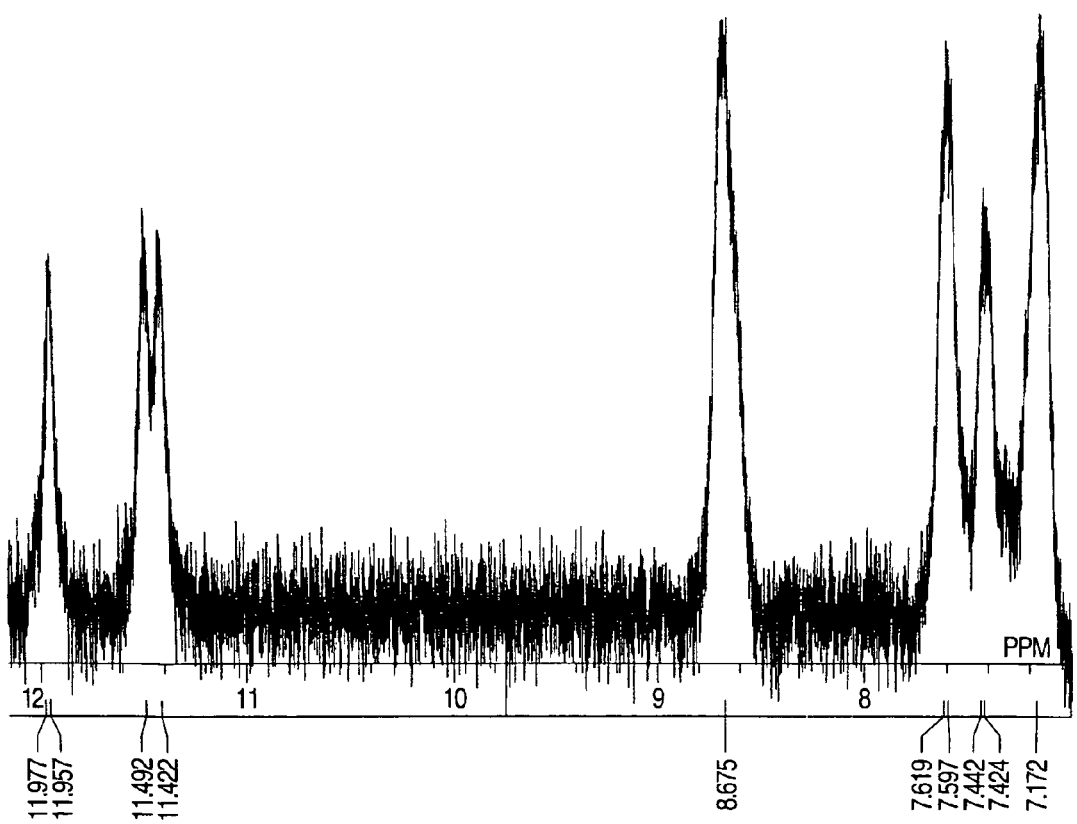
FIG. 7 is an NMR chart showing 6-fluoroindole trimer according to Example 4.
Figure 8:
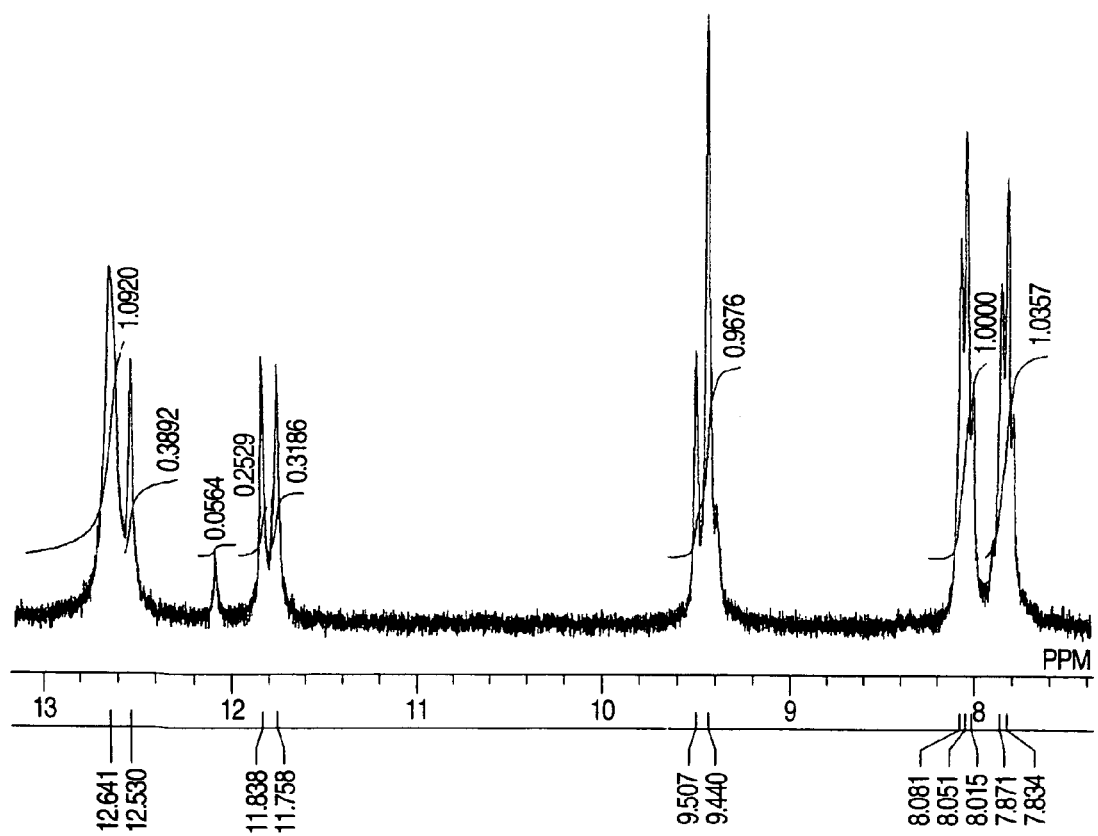
FIG. 8 is an NMR chart showing indole-5-carboxylic acid trimer according to Example 12.

The indole derivatives (a) of formula (1) used in the methods of the present invention include, for instance, indole; alkyl group-substituted indoles, such as 4-methyl indole, 5-methylindole, 6-methylindole, 7-methylindole, 4-ethylindole, 5-ethylindole, 6-ethylindole, 7-ethylindole, 4-n-propylindole, 5-n-propylindole, 6-n-propylindole, 7-n-propylindole, 4-iso-propylindole, 5-iso-propylindole, 6-iso-propylindole, 7-iso-propylindole, 4-n-butylindole, 5-n-butylindole, 6-n-butylindole, 7-n-butylindole, 4-sec-butylindole, 5-sec-butylindole, 6-sec-butylindole, 7-sec-butylindole, 4-t-butylindole, 5-t-butylindole, 6-t-butylindole, 7-t-butylindole; alkoxy group substituted indoles, such as 4-methoxyindole, 5-methoxyindole, 6-methoxyindole, 7-methoxyindole, 4-ethoxyindole, 5-ethoxyindole, 6-ethoxyindole, 7-ethoxyindole, 4-n-propoxyindole, 5-n-propoxyindole, 6-n-propoxyindole, 7-n-propoxyindole, 4-iso-propoxyindole, 5-iso-propoxyindole, 6-iso-propoxyindole, 7-iso-propoxyindole, 4-n-butoxyindole, 5-n-butoxyindole, 6-n-butoxyindole, 7-n-butoxyindole, 4-sec-butoxyindole, 5-sec-butoxyindole, 6-sec-butoxyindole, 7-sec-butoxyindole, 4-t-butoxyindole, 5-t-butoxyindole, 6-t-butoxyindole, 7-t-butoxyindole; acyl group-substituted indoles, such as 4-acetylindole, 5-acetylindole, 6-acetylindole, and 7-acetylindole; aldehyde group-substituted indoles, such as indole-4-carbaldehide, indole-5-carbaldehide, indole-6-carbaldehide, and indole-7-carbaldehide; carboxyl group-substituted indoles, such as indole-4-carboxylic acid, indole-5-carboxylic acid, indole-6-carboxylic acid, and indole-7-carboxylic acid; carboxylic ester group-substituted indoles, such as methyl indole-4-carboxylate, methyl indole-5-carboxylate, methyl indole-6-carboxylate, and methyl indole-7-carboxylate; sulfonic group-substituted indoles, such as indole-4-sulfonic acid, indole-5-sulfonic acid, indole-6-sulfonic acid, and indole-7-sulfonic acid; sulfonic ester group-substituted indoles, such as methyl indole-4-sulfonate, methyl indole-5-sulfonate, methyl indole-6-sulfonate, methyl indole-7-sulfonate; cyano group-substituted indoles, such as indole-4-carbonitrile, indole-5-carbonitrile, indole-6-carbonitrile, and indole-7-carbonitrile; hydroxy group-substituted indoles, such as 4-hydroxyindole, 5-hydroxyindole, 6-hydroxyindole, and 7-hydroxyindole; nitro group-substituted indoles, such as 4-nitroindole, 5-nitroindole, 6-nitroindole, 7-nitroindole; amino group-substituted indoles, such as 4-aminoindole, 5-aminoindole, 6-aminoindole, and 7-aminoindole; amide group-substituted indoles, such as 4-carbamoylindole, 5-carbamoylindole, 6-carbamoylindole, and 7-carbamoylindole; and halogen group-substituted indoles such as 4-fluoroindole, 5-fluoroindole, 6-fluoroindole, 7-fluoroindole, 4-chloroindole, 5-chloroindole, 6-chloroindole, 7-chloroindole, 4-bromoindole, 5-bromoindole, 6-bromoindole, 7-bromoindole, 4-iodoindole, 5-iodoindole, 6-iodoindole, and 7-iodoindole.

Among these, the acyl group-substituted indoles, carboxylic group-substituted indoles, cyano group-substituted indoles, nitro group substituted indoles, fluoro group-substituted indoles are preferable in actual use.

The oxidants (B) used in the present invention include, but not limited to, for instance, ferric chloride hexahydrate, ferric chloride andydrate, ferric nitrate enneahydrate, ferric sulfate n-hydrate, ferric sulfate ammonium dodecahydrate, ferric perchlorate n-hydrate, ferric tetrafluoroborate, cupric chloride, ferric nitrate, cupric sulfate, cupric tetrafluoroborate, nitrosonium tetrafluoroborate, ammonium persulfate, sodium persulfate, potassium persulfate, potassium periodate, ozone, potassium hexacyano ferrate, tetra-ammonium cerium (IV) sulfate dehydrate, ferric chloride hexahydrate, bromine, and iodine. Preferably the oxidant (B) is selected from the group consisting of ferric chloride hexahydrate, ferric chloride anhydrate, ferric nitrate enneahydrate, ferric sulfate n-hydrate, ferric ammonium sulfate dodecahydrate, ferric perchlorate n-hydrate, ferric tetrafluoroborate, cupric chloride, ferric nitrate, cupric sulfate, cupric tetrafluoroborate, nitrosonium tetrafluoroborate, ammonium persulfate, sodium persulfate, potassium persulfate, potassium periodate, hydrogen peroxide, and ozone. More preferably, the oxidant (B) is elected from the group consisting of ferric chloride hexahydrate, ferric chloride anhydrate, ferric nitrate enneahydrate, ferric sulfate n-hydrate, ferric sulfate ammonium dodecahydrate, ferric perchlorate n-hydrate, ferric tetrafluoroborate, cupric chloride, ferric nitrate, cupric sulfate, cupric tetrafluoroborate, ammonium persulfate, and ozone, and of these, ferric chloride hexahydrate, ferric chloride anhydrate, ferric nitrate enneahydrate, ferric sulfate n-hydrate, ferric sulfate ammonium dodecahydrate, ferric perchlorate n-hydrate, ferric tetrafluoroborate, ammonium persulfate, and ozone are most preferable in actual use. It should be noted that any of these oxidants may be used singly or in combination with other one or more oxidants with an arbitrary ratio.

A molar ratio of the indole derivative (A) to oxidant (B) [(A):(B)] employed in the present invention is in the range of 1:0.5 to 1:100, and preferably in the range from 1:1 to 1:50. When a percentage of the oxidant is low, the reactivity becomes lower and the raw material may remain, and on the contrary, when the percentage is too high, the produced trimer is overoxidized, which may in turn cause degradation of the product.

The organic solvents (C) used in the present invention include, but not limited to, methanol, ethanol, isopropanol, acetone, acetonitrile, propionitrile, tetrahydrofuran, 1,4-dioxane, methyl isobutyl ketone, methyl ethyl ketone, γ-butyl lactone, propylene carbonate, sulfolane, nitromethane, N,N-dimethyl formamide, N-methyl acetamide, dimethyl sulfoxide, dimethyl sulfone, N-methyl pyrrolidone, benzene, toluene, xylene, methylene chloride, chloroform, and dichloroethane. Each of these solvents may be used singly or in combination with one or more other solvents. Of these solvents, acetone, acetonitrile, 1,4-dioxane, γ-butyl lactone, and N,N-dimethyl formamide are preferable, and especially acetonitrile is practically the most preferable.

Further in the present invention, a concentration of the indole derivative (A) against during the reaction is more than 0.01% by weight, preferably in the range from 0.1 to 50% by weight, and more preferably in the range from 1 to 30% by weight, in the organic solvent (C).

In the method according to the present invention, the reaction is preferably performed in the state where water and the organic solvent (C) coexist. The preferable molar ratio in use of the indole derivative (A) to water [(A):water] is in the range from 1:1000 to 1000:1, and more preferably in the range from 1:100 to 100:1. In a case where the oxidant contains crystal water, however, also the crystal water is weighed as a portion of the water content. In this respect, if the water content is too low, the reaction may go out of control and the trimer may be overoxidized to cause degradation of the structure, and, at the same time, $X^{a-}$ acting as a dopant for the trimer may not be efficiently doped to lower its conductivity. On the contrary, if the water content is too high, the oxidation reaction may not proceed well to lower the reaction yield.

The reaction temperature in the production method according to the present invention is preferably in the range from −20 to 120° C., and more preferably in the range from 0 to 100° C. When the reaction temperature is −20° C. or lower, the oxidative becomes extremely slow, and the $X^{a-}$ acting as a dopant for the trimer may not be efficiently doped to lower its conductivity. On the other hand, when the reaction temperature is 120° C. or higher, the structure of the trimer degrades to lower its conductivity.

Although any reaction method may be employed as the production method according to the present invention, the method of adding a solution of the oxidant (B) and water or a solution of the oxidant (B), water, and the organic solvent (C) into a solution of the indole derivative (A) and the organic solvent (C) is preferably employed. In this method, the oxidant (B), water, and/or the organic solvent (C) may be added either as in admixture or separately. Although there is no specific restriction on a time in which the addition of the oxidant (B) and/or water and/or the organic solvent (C) is carried out, but typically the time is 15 minutes or more, preferably in the range from 30 to 720 minutes, and more preferably in the range from 30 to 180 minutes. When the oxidant (B) and water and/or the organic solvent (C) are added in a time less than 15 minutes, progress of the oxidative reaction may become extremely slow due to the effect of water included in the reaction mixture to lower the yield. If an extremely long time is spent for the step of adding, only the productivity will drop, and any improvement in the effect cannot be obtained.

There is not specific restriction on pH of the reaction liquid in the present invention, but the reaction is preferably performed under the acidic condition, at a pH lower than 7, more preferably at a pH of 2 or lower, and most preferably at a pH lower than pH. If the reaction is performed at a pH higher than 7, the oxidative reaction becomes slow to lower the yield, and, at the same time, the $X^{a-}$ acting as a dopant for the trimer may not be efficiently doped and, thus the conductivity of the obtained trimer tends to be lowered.

The $X^{a-}$ in the indole derivative trimer obtained by the production method according to the present invention is a dopant, which is an anion of protonic acid originated from the oxidant in the polymerization. More specifically, the $X^{a-}$ is a monovalent to trivalent anion, such as chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, p-toluene sulfonate ion, trifluoroacetate ion, and trifluoromethane sulfonate ion, and is preferably a monovalent or bivalent anion, such as chlorine ion, sulfate ion, and fluoroborate ion. Most preferably the $X^{a-}$ is a monovalent anion, such as chlorine ion. For instance, when polymerization is performed by selecting ferric chloride anhydrate as the oxidant (B), the dopant $X^{a-}$ in the indole derivative trimer is chlorine ion, and when polymerization is performed by using cupric trifluoroacetate, the dopant $X^{a-}$ is trifluoroacetate ion.

The indole derivative trimer obtained by the production method according to the present invention is a doped type-indole derivative trimer except when hydrogen peroxide or ozone is used as an oxidant, and a molar ratio of the dopant $X^{a-}$ to the trimer unit, m (dope ratio) is in the range from 0.001 to 0.5. When hydrogen peroxide or ozone is used as an oxidant, an undoped type-indole trimer with a dope ratio m=0 is obtained.

When the indole derivative trimer according to the present invention is used as an electric pole of a cell, a capacitor, or the like, it is indispensable that the cycle characteristic is excellent. Whether the cycle characteristic is excellent or not depends on a type of the dopant $X^{a-}$. The dopant $X^{a-}$ giving the indole derivative with the excellent cycle characteristic is a monovalent to trivalent anion, preferably a monovalent to bivalent anion, and most preferably a chlorine ion which is a monovalent anion, or a sulfate ion which is a bivalent anion.

With the indole derivative trimer which can be obtained by the reaction method performed under the existence of the $X^{a-}$ component according to the present invention, the undoped type-indole derivative trimer (namely indole derivative trimer with the dope ratio m of 0 (zero)) can be readily formed by the method known as a process for undoping various conductive polymers or charge transfer complex, namely by the method in which the dopant $X^{a-}$ is removed by suspending a conductive polymer or a charge transfer complex in an alkaline solution, such as ammonia water, sodium hydrate, and lithium hydrate. The undoped type-indole derivative trimer can easily be transformed to a doped type-indole derivative trimer with a desired dope ratio for a given dopant by treating it with a required quantity of a required type of doping agent. For instance, the doped type-indole derivative trimer polymerized with an oxidant having a counter ion other than a chlorine ion can be transformed a chlorine-doped type-indole derivative trimer by dedoping the indole derivative trimer as polymerized with a sodium hydrate solution to obtain a undoped type-indole derivative trimer and then re-suspending the resultant undoped type-indole derivative trimer in aqueous hydrochloric acid solution.

Especially 4-nitroindole derivative trimer, 6-nitroindole derivative trimer, 7-nitroindole derivative trimer, indole-4-carbonitrile derivative trimer, indole-6-carbonitrile derivative trimer, indole-7-carbonitrile derivative trimer, indole-4-carboxylic acid derivative trimer, indole-6-carboxylic acid derivative trimer, indole-7-carboxylic acid derivative trimer, indole-4-carbaldehyde derivative trimer, indole-5-carbaldehyde derivative trimer, indole-6-carbaldehyde derivative trimer, indole-7-carbaldehyde derivative trimer, 4-carbamoyl indole derivative trimer, 5-carbamoyl indole derivative trimer, 6-carbamoyl indole derivative trimer, 7-carbamoyl indole derivative trimer, 4-bromoindole derivative trimer, 6-bromoindole derivative trimer, 7-bromoindole derivative trimer, 4-fluoroindole derivative trimer, 6-fluoroindole derivative trimer, 7-fluoroindole derivative trimer, 4-acetylindole derivative trimer, 5-acetylindole derivative trimer, 6-acetylindole derivative trimer, and 7-acetylindole derivative trimer can conveniently be produced by the production method according to the present invention with a high yield and in an industrial scale, and these indole derivative trimers have a higher oxidation-reduction potential as compared to those known in the conventional technology and also have excellent cycle characteristics.

Although these novel indole derivative trimers obtained by the production method according to the present invention are doped type with the dope ratio m in the range from 0.001 to 0.5, they can easily be transformed to the corresponding undoped type-indole derivative trimers [(with the dope ratio of 0 (zero)] by the undoping method described above, and further by selecting a desired dopant and a desired dope ratio in re-doping, doped type-indole derivative trimer having the desired characteristics can be prepared.

Further the dope ratio and conductivity can be improved, by performing a doping treatment to the resultant indole derivative trimer after the end of the reaction using an acidic solution. Specifically, the acidic solution is, for instance, an aqueous solution comprising an inorganic acid such as hydrochloric acid, sulfuric acid, and nitric acid; an organic acid such as p-toluene sulfonic acid, camphorsulfonic acid, benzoic acid, or derivatives having the framework of these acids; or polymer acids such as polystyrene sulfonic acid, polyvinyl sulfonic acid, poly(2-acrylamide-2-methyl propane) sulfonic acid, polyvinyl sulfuric acid or derivatives having the framework of the acids above; or a mixture solution of water and an organic solvent comprising the same. It is to be noted that these inorganic or organic acids, and polymer acids may be used singly or with any one or more of the others.

In addition, the indole derivative trimers obtained by the method according to the present invention may be used as conductive compositions consisting of indole derivative trimers themselves or as conductive compositions comprising the indole derivative trimer kneaded in or conjugated to various types of carbon as coadjuvants for improving the conductivity, or to colloidal silica, or various types of binders as an additive. Of these, conductive compounds obtained by using indole derivative trimer particles having a diameter in the range from 0.1 to 50 μm are especially preferable. Although a method of adjusting the particle diameter is not particularly limited, typically the adjustment is carried out by spray drying after slurry cleaning, or pulverizing dried powder of the compositions in a mortar or by a ball mill or a blender, or by the supersonic vibration processing. When the conductive compositions above are molded by using the indole derivative trimers with the particle diameter of over 50 μm, the mechanical strength of the molded products is apt to be lower.

Further when the indole derivative trimer according to the present invention has a laminated structure, it shows the conductive property. Especially the indole derivative trimer preferably has the laminated structure with an interlaminar spacing in the range from 0.1 to 0.6 nm, and more preferably in the range from 0.35 to 0.60 nm. Generally, compositions having a ultra-fine laminated structure have excellent physical properties, such as solidity, strength, and heat resistance. When the interlaminar spacing is less than 0.1 nm, the laminated structure is apt to be unstable. When the interlaminar spacing is more than 0.6 nm, the electron hopping conduction among the trimers is adversely affected, to lower the conductivity.

EXAMPLES

The present invention is described below in further detail with reference to the examples, but the present invention is not limited to these examples.

In the examples described below, the NMR measurement was performed with the JNX GX-270 produced by NIHON DENSHI K. K., while the IR spectrum was measured by the KBγ method with a device (Model 1600) produced by Perkin Elmer Co. The elemental analysis was performed with the EA1110 produced by Thermo Quest Co. The conductivity was measured (by the four terminal method) with the resitivity meter Loresta EP Model MCP-T350 produced by MITSUBISHI KAGAKU k.k. The electrochemical measurement was performed with the potentiostat/galvanostat NP-G-1051EH as well as with the potential scanner ES-512A. Further the X-ray diffraction analysis (XRD) was performed with the RINT-1100 (tube ball: $CuK_\alpha$ X-ray) produced by RIGAKU DENKI k.k., and the particle diameter distribution was measured with the LS130 produced by the COULTER Corp.

Example 1

10 ml of acetonitrile was poured into a 200 ml three-neck flask, and 1.42 g of indole-5-carbonitrile was dissolved therein. On the other hand, the oxidant solution was prepared by dissolving 16.2 g of ferric chloride anhydrate and 5.4 g of water in 40 ml of acetonitrile and agitating the resultant mixture for 10 minutes. Then the prepared oxidant solution was dripped into the indole-6-carbonitrile solution for 30 minutes, which was then agitated for 10 hours at the temperature of 60° C. Color of the reaction solution changed from yellow to green with slight heat generation, and the pH was less than 1. After the end of the reaction, the reaction solution was suction-filtered with a perforated funnel, washed with acetonitrile and then methanol, and the filtrate was dried to obtain 1.01 g of 6,11-dihydro-5H-diindolo[2,3-a:2',3'-c] carbazole-3,8,13-tricarbonitrile (indole-6-carbonitrile trimer) with a green color (yield: 71%). The resultant trimer was pressure-molded with a tablet molding machine. The mold was cut into a piece with the diameter of 10 mm and thickness of 1 mm. A conductivity thereof was then measured by the four terminal method, and found to be 0.95 S/cm. The result of elemental analysis was: $<C_{9.00}H_{4.04}N_{1.98}Cl_{0.15}>_3$.

Example 2

10 ml of acetonitrile was poured into a 200 ml three-neck flask, and 1.42 g of indole-5-carbonitrile was dissolved therein. On the other hand, an oxidant solution was prepared by dissolving 16.2 g of ferric chloride anhydrate and 5.4 g of water in 40 ml of acetonitrile and agitating the resultant mixture for 10 minutes. Then the prepared oxidant solution was dripped into the indole-5-carbonitrile solution for 30 minutes, which was then agitated for 10 hours at the temperature of 60° C. Color of the reaction solution changed from yellow to green with slight heat generation, and the pH was less than 1. After the end of the reaction, the reaction solution was suction-filtered with a perforated funnel, and the filtrate was washed with acetonitrile and then methanol, and then dried to obtain 1.22 g of 6,11-dihydro-5H-diindolo[2,3-a:2', 3'-c] carbazole-2,9,14-tricarbonitrile (indole-5-carbonitrile trimer) with a green color (yield: 86%). The resultant trimer was pressure-molded with a tablet molding machine and the mold was cut into a piece with the diameter of 10 mm and thickness of 1 mm. A conductivity thereof was measured by the four terminal method and found to be 0.50 S/cm. The result of elemental analysis was: $<C_{9.00}H_{4.03}N_{1.97}Cl_{0.10}>_3$. Further the result of X-ray diffraction crystal analysis indicated that the interlaminar spacing was 0.44 nm.

Example 3

Polymerization was performed in the same way as of Example 2 except that 6-nitroindole was used in place of indole-5-carbonitrile. pH of the reaction solution was less than 1. 1.12 g of 6,11-dihydro-3,8,13-trinitro-5H-diindolo [2,3-a:2',3'-c] carbazole (6-nitroindole trimer) with a dark blue color was obtained (yield: 79%). The resultant trimer was pressure-molded with a tablet molding machine and the mold was cut into a piece with the diameter of 10 mm and thickness of 1 mm. A conductivity thereof was measured by the four terminal method and found to be 0.83 S/cm. The result of elemental analysis was: $<C_{8.00}H_{4.00}N_{2.02}O_{1.97}Cl_{0.15}>_3$.

Example 4

Polymerization was performed in the same way as of Example 2 except that 6-fluoroindole was used in place of indole-5-carbonitrile. pH of the reaction solution was less than 1. 1.01 g of 3,8,13-trifluoro-6,11-dihydro-5H-diindolo [2,3-a:2',3'-c] carbazole (6-fluoroindole trimer) with a dark blue color was obtained(yield: 71%). The resultant trimer was pressure-molded with a tablet molding machine and the mold was cut into a piece with the diameter of 10 mm and thickness of 1 mm. A conductivity thereof was measured by the four terminal method and found to be 0.76 S/cm. The result of elemental analysis was: $<C_{8.00}H_{4.01}N_{0.99}F_{0.97}Cl_{0.16}>_3$. Further the result of X-ray diffraction crystal analysis indicated that the inter-layer space was 0.38 nm.

Example 5

Polymerization was performed in the same way as of Example 2 except that cupric chloride anhydrate was used in place of ferric chloride anhydrate. pH of the reaction solution was less than 1. 1.12 g of 6,11-dihydro-5H-diindolo [2,3-a: 2',3'-c] carbazole-2,9,14-tricarbonitrile (indole-5-carbonitrile trimer) with a green color was obtained (yield: 79%). The resultant trimer was pressure-molded with a tablet molding machine and the mold was cut into a piece with the diameter of 10 mm and thickness of 1 mm. A conductivity thereof was measured by the four terminal method and found to be 0.55 S/cm. The result of elemental analysis was: $<C_{9.00}H_{4.03}N_{1.97}Cl_{0.11}>_3$.

Example 6

15 ml of acetone was poured into a 200 ml three-neck flask, and 1.62 g of 5-fluoroindole was dissolved therein. On the other hand, preparation of an oxidant solution was performed by dissolving 32.2 g of cupric chloride anhydrate and 12.9 g of water in 55 ml of acetone and agitating the mixture for 5 minutes. Then the prepared oxidant solution was dripped into the 5-fluoroindole solution for two hours and the resultant mixture solution was agitated for 5 hours at the temperature of 30° C. Color of the reaction solution changed from white to dark blue with slight heat generation. pH of the reaction solution was less than 1. After the end of the reaction, the reaction liquid was suction-filtered with a perforated funnel, and the filtrate was washed with acetone and then methanol and dried to obtain 1.04 g of 2,9,14-trifluoro-6,11-dihydro-5H-diindolo [2,3,-a:2',3'-c] carbazole (5-fluoroindole trimer) (yield: 64%). The resultant trimer was pressure-molded with a tablet molding machine and the mold was cut into a piece with the diameter of 10 mm and thickness of 1 mm. A conductivity thereof was measured by the four terminal method and found to be 0.88 S/cm. The result of elemental analysis was: $<C_{8.00}H_{3.95}N_{1.10}F_{0.96}Cl_{0.10}>_3$.

Example 7

Polymerization was performed in the same way as that employed in Example 6 except that indole-5-carboxylic acid was used in place of 5-fluoroindole. pH of the reaction liquid was less than 1. 1.28 g of 6,11-dihydro-5H-diindolo [2,3-a: 2',3'-c] carbazole-2,9,14-tricarboxylic acid (indole-5-carboxylic acid trimer) was obtained (yield: 79%). The resultant trimer was pressure-molded with a tablet molding machine and the mold was cut into a piece with the diameter of 10 mm and thickness of 1 mm. A conductivity thereof was measured by the four terminal method and found to be 0.41 S/cm. The result of elemental analysis was: $<C_{9.00}H_{4.90}N_{1.09}O_{1.98}Cl_{0.11}>_3$. Further the result of X-ray diffraction crystal analysis indicated that the interlaminar spacing was 0.48 nm.

Example 8

15 ml of dimethyl formamide was poured into a 200 ml three-neck flask, and 1.42 g of indole was dissolved therein. On the other hand, preparation of an oxidant solution was performed by dissolving 11.4 g of ammonium persulfate and 2.70 g of water and agitating the resultant mixture for 15 minutes. Then the prepared oxidant solution was dripped into the indole solution for 60 minutes, and the resultant mixture solution was agitated for 12 hours at the temperature of 50° C. Color of the reaction liquid changed from yellow to blue-green with slight heat generation. pH of the reaction solution was less than 1. After the end of the reaction, the reaction solution was suction-filtered with a Perforated funnel, and the filtrate was washed with dimethylformamide and then with methanol and dried to obtain 1.26 g of 6,11-dihydro-5H-diindolo [2,3-a:2',3'-c] carbazole (indole trimer) with a blue-green color (yield: 96%). The resultant trimer was pressure-molded with a tablet molding machine and the mold was cut into a piece with the diameter of 10 mm and thickness of 1 mm. A conductivity thereof was measured by the four terminal method and found to be 0.40 S/cm. The result of elemental analysis was: $<C_{8.00}H_{4.91}N_{0.98}(SO_4)_{0.07}>_3$.

Example 9

Polymerization was performed in the same way as that employed in Example 2 except that 5-acetyl indole was used in place of indole-5-carbonitrile. pH of the reaction solution was less than 1. 1.01 g of 2,9,14-triacetyl-6,11-dihydro-5H-diindolo [2,3-a:2',3'-c] carbazole (5-acetyl indole trimer) with a green color was obtained (yield: 71%). The resultant trimer was pressure-molded with a tablet molding machine and the mold was cut into a piece with the diameter of 10 mm and thickness of 1 mm. A conductivity thereof was measured by the four terminal method and found to be 0.76 S/cm. The result of elemental analysis was: $<C_{10.00}H_{6.97}N_{0.99}O_{0.99}Cl_{0.14}>_3$.

Example 10

Polymerization was performed in the same way as that employed in Example 2 except that 5.4 g of water was not added. pH of the reaction liquid was less than 1. 1.22 g of 6,11-dihydro-5H-diindolo [2,3-a:2',3'-c] carbazole-2,9,14-tricarbonitrile (indole-5-carbonitrirle trimer) with a green-brown color was obtained (yield: 86%). The resultant trimer was pressure-molded with a tablet molding machine and the mold was cut into a piece with the diameter of 10 mm and thickness of 1 mm. A conductivity thereof was measured by the four terminal method and found to be 0.40 S/cm. The result of elemental analysis was: $<C_{9.00}H_{4.01}N_{1.99}Cl_{0.07}>_3$.

Example 11

15 ml of acetone was poured into a 200 ml three-neck flask, and 1.35 g of 5-fluoroindole was dissolved therein. On the other hand, preparation of an oxidant solution was performed by dissolving 33.6 g of cupric chloride anhydrate and 13.5 g of water in 55 ml of acetone and then agitating the resultant mixture for 5 minutes. Then the prepared oxidant solution was dripped into the 5-fluoroindole solution over 2 hours, and the resultant mixture was agitated for 5 hours at the temperature of 40° C. Color of the reaction solution changed from white to dark blue with slight heat generation. pH of the reaction solution was less than 1. After the end of the reaction, the reaction solution was suction-filtered with a Perforated funnel, and the filtrate was washed with acetone and then methanol, and was dried to obtain 0.86 g of 2,9,14-trifluoro-6,11-dihydro-5H-diindolo [2,3-a:2',3'-c] carbazole (5-fluoroindole trimer) (yield: 64%). The resultant trimer was pressure-molded with a tablet molding machine and the mold was cut into a piece with the diameter of 10 mm and thickness of 1 mm. A conductivity thereof was measured by the four terminal method and to be 0.88 S/cm. The result of elemental analysis was: $<C_{8.00}H_{3.95}N_{1.10}Cl_{0.10}>_3$.

Example 12

Polymerization was performed in the same way as that employed in Example 11 except that indole-5-carboxylic acid was used in place of 5-fluoroindole used in Example 11. pH of the reaction liquid was less than 1. 1.07 g of 6,11-dihydro-5H-diindolo [2,3-a:2',3'-c] carbazole-2,9,14-tricarboxylic acid (indole-5-carboxylic acid trimer) was obtained (yield: 79%). The resultant trimer was pressure-molded with a tablet molding machine and the mold was cut into a piece with the diameter of 10 mm and thickness of 1 mm. A conductivity thereof was measured by the four terminal method and found to be 0.41 S/cm. The result of elemental analysis was: $<C_{9.00}H_{4.90}N_{1.09}O_{1.98}Cl_{0.11}>_3$. Further the result of X-ray diffraction crystal analysis indicated that the interlaminar spacing was 0.48 nm.

Example 13

Polymerization was performed in the same way as that employed in Example 11 except that indole-7-carbaldehyde was used in place of 5-fluoroindole. pH of the reaction solution was less than 1. 0.96 g of 6,11-dihydro-5H-diindolo [2,3-a:2',3'-c] carbazole-4,7,12-tricarbaldehyde (indole-7-carbaldehyde trimer) was obtained (yield: 71%). The resultant trimer was pressure-molded with a tablet molding machine and the mold was cut into a piece with the diameter of 10 mm and thickness of 1 mm. A conductivity thereof was measured by the four terminal method and found to be 0.70 S/cm. The result of elemental analysis was: $<C_{9.00}H_{4.90}N_{1.09}O_{0.98}Cl_{0.14}>_3$.

Example 14

15 ml of chloroform was poured into a 200 ml three-neck flask, and 1.17 g indole was dissolved therein. On the other hand, preparation of an oxidant solution was performed by dissolving 11.4 g of ammonium persulfate and 2.70 of water in 60 ml of chloroform and agitating the mixture for 15 minutes. Then the prepared oxidant solution was dripped over 60 minutes into the indole solution, and the resultant mixture was agitated for 12 hours at the temperature of 40° C. Color of the reaction solution changed from yellow to blue-green with slight heat generation. pH of the reaction liquid was less than 1. After the end of the reaction, the reaction solution was suction-filtered with a Perforated funnel, and the filtrate was washed with chloroform and then methanol, and was dried to obtain 1.04 g of 6,11-dihydro-5H-diindolo [2,3-a:2',3'-c] carbazole (indole trimer) (yield: 96%). The resultant trimer was pressure-molded with a tablet molding machine and the mold was cut into a piece with the diameter of 10 mm and thickness of 1 mm. A conductivity thereof was measured by the four terminal method and found to be 0.40 S/cm. The result of elemental analysis was: $<C_{8.00}H_{4.91}N_{0.98}(SO_4)_{0.07}>_3$. Further the result of X-ray diffraction crystal analysis indicated that the interlaminar spacing was 0.37 nm.

Example 15

15 ml of acetonitrile was poured into a 200 ml three-neck flask, and 1.61 g of indole-5-carboxylic acid was dissolved therein. On the other hand, preparation of an oxidant solution was performed by dissolving 47.4 g of cupric tetrafluoroborate n-hydrate (Cu content: 20%) in 100 ml of acetonitrile and agitating the mixture for 15 minutes. pH of the reaction solution was less than 1. Then the prepared oxidant solution was dripped over 60 minutes into the indole-5-carboxylic acid solution, and the resultant mixture solution was agitated for 5 hours at the temperature of 30° C. Color of the reaction solution changed from yellow to blue-green with slight heat generation. After the end of the reaction, the reaction liquid was suction-filtered with a perforated funnel, and the filtrate was washed with acetonitrile and then methanol, and was dried to obtain 1.43 g of 6,11-dihydro-5H-diindolo [2,3-a:2', 3'-c] carbazole-2,9,14-tricarboxylic acid (indole-5-calboxylic acid trimer) with a blue-green color (yield: 89%). The resultant trimer was pressure-molded with a tablet molding machine and the mold was cut into a piece with the diameter of 10 mm and thickness of 1 mm. A conductivity thereof was measured by the four terminal method, and found to be 0.40 S/cm. The result of elemental analysis was: $<C_{9.00}H_{4.95}N_{0.98}O_{1.98}Cl_{0.13}>_3$.

Example 16

15 ml of acetonitrile was poured into a 200 ml three-neck flask, and 1.59 g of 6-acetylindole was dissolved therein. On the other hand, preparation of an oxidant solution was performed by dissolving 16.2 g of ferric chloride anhydrate and 5.4 g of water in 100 ml of acetonitrile and agitating the resultant mixture solution for 15 minutes. Then, the prepared 6-acetyl indole solution was dripped over 60 minutes into the oxidant solution, and the resultant mixture solution was agitated for 5 hours at the temperature of 30° C. Color of the reaction solution changed from yellow to blue-green with slight heat generation. pH of the reaction solution was less than 1. After the end of the reaction, the reaction liquid was suction-filtered with a perforated funnel, and the filtrate was washed with acetonitrile and then methanol, and was dried to obtain 1.11 g of 3,8,13-triacetyl-6,11-dihydro-5H-diindolo [2,3-a:2',3'-c] carbazole (6-acetyl indole trimer) with a blue-green color (yield: 70%). The resultant trimer was pressure-molded with a tablet molding machine and the mold was cut into a piece with the diameter of 10 mm and thickness of 1 mm. A conductivity thereof was measured by the four terminal method and found to be 0.90 S/cm. The result of elemental analysis was: $<C_{10.00}H_{6.99}N_{0.98}O_{1.98}Cl_{0.10}>_3$.

Example 17

1.07 g of the indole-5-carboxylic acid trimer synthesized in Example 12 was suspended in 30 ml of 10% aqueous sulfuric acid-methanol solution, and the suspension was agitated for 2 hours at the temperature of 25° C. The suspension was suction-filtered with a perforated funnel, washed with methanol and dried to obtain 1.00 g of 6,11-dihydro-5H-diindolo [2,3-a:2',3'-c] carbazole-2,9,14-tricarboxylic acid (indole-5-carboxylic acid trimer) with a light green color. The resultant trimer was pressure-molded with a tablet molding machine and the mold was cut into a piece with the diameter of 10 mm and thickness of 1 mm. A conductivity thereof was measured by the four terminal method and found to be 0.55 S/cm. The result of elemental analysis was: $<C_{9.00}H_{4.90}N_{1.09}O_{1.98}Cl_{0.03}(SO_4)_{0.12}>_3$.

Example 18

0.96 g of the indole-7-carbaldehyde trimer synthesized in Example 13 was suspended in 50 ml of 5% p-toluene sulfonic acid (described as pTs hereinafter), and the suspension was agitated for 2 at under the temperature of 25° C. The suspension was suction-filtered with a Perforated funnel, and was washed with methanol, and was dried to obtain 0.90 g of 6,11-dihydro-5H-diindolo [2,3-a:2',3'-c] carbazole-4,7,12-tricarbardehyde (indole-7-carbaldehyde trimer) with a light green color. The resultant trimer was pressure-molded with a tablet molding machine and the mold was cut into a piece with the diameter of 10 mm and thickness of 1 mm. A conductivity thereof was measured by the four terminal method and found to be 0.95 S/cm. The result of elemental analysis indicated was: $<C_{9.00}H_{4.90}N_{1.09}O_{0.98}Cl_{0.02}(pTs)_{0.10}>_3$.

Example 19

1.11 g of the 6-acetyl indole synthesized in Example 16 was suspended in 50 ml of 10% polyvinyl sulfonic acid (described as PVs hereinafter), and the suspension was agitated for 2 hours at the temperature of 25° C. The suspension was suction-filtered with a Perforated funnel and was dried to obtain 1.05 g of 3,8,13-triacetyl-6,11-dihydro-5H-diindolo [2,3-a:2',3'-c] carbazole (6-acetyl indole trimer) with a blue-green color. The resultant trimer was pressure-molded with a tablet molding machine and the mold was cut into a piece with the diameter of 10 mm and thickness of 1 mm. A conductivity thereof was measured by the four terminal method and found to be 0.88 S/cm. The result of elemental analysis was: $<C_{10.00}H_{6.99}N_{0.98}O_{0.98}Cl_{0.02}(PVs)_{0.14}>_3$.

Example 20

Polymerization was performed in the same way as that employed in Example 2 except that 4-nitroindole was used in place of indole-5-carbonitrile. pH of the reaction solution was less than 1. 1.15 g of 6,11-dihydro-1,10,15-trinitro-5H-diindolo [2,3-a:2',3'-c] carbazole (4-nitroindole trimer) with a dark blue color was thus-obtained (yield: 81%). The resultant trimer was pressure-molded with a tablet molding machine and the mold was cut into a piece with the diameter of 10 mm and thickness of 1 mm. A conductivity thereof was measured by the four terminal method and found to be 0.58 S/cm. The result of elemental analysis was: $<C_{8.00}H_{4.00}N_{2.01}O_{1.98}Cl_{0.16}>_3$.

Example 21

Polymerization was performed in the same way as that employed in Example 2 except that 7-nitroindole was used in place of the indole-5-carbonitrile. pH of the reaction solution was less than 1. 1.09 g of 6,11-dihydro-4,7,12-trinitro-5H-diindolo [2,3-a:2',3'-c] carbazole (7-nitroindole trimer) with a dark blue color was thus-obtained (yield: 77%). The resultant trimer was pressure-molded with a tablet molding machine and the mold was cut into a piece with the diameter of 10 mm and thickness of 1 mm. A conductivity thereof was measured by the four terminal method and found to be 0.85 S/cm. The result of elemental analysis was: $<C_{8.00}H_{3.99}N_{2.01}O_{2.01}Cl_{0.12}>_3$.

Example 22

Polymerization was performed in the same way as that employed in Example 2 except that indole-4-carbonitrile was used in place of indole-5-carbonitrile used. pH of the reaction solution was less than 1. 1.10 g of 6,11-dihydro-5H-diindolo [2,3-a:2',3'-c] carbazole-1,10,15-tricarbonitrile (indole-4-carbonitrile trimer) with a dark blue color was thus-obtained (yield: 77%). The resultant trimer was pressure-molded with a tablet molding machine and the mold was cut into a piece with the diameter of 10 mm and thickness of 1 mm. A conductivity thereof was measured by the four terminal method and found to be 0.75 S/cm. The result of elemental analysis was: $<C_{9.00}H_{4.02}N_{1.97}Cl_{0.10}>_3$.

Example 23

Polymerization was performed in the same method as that employed in Example 2 except that indole-7-carbonitrile was used in placed of the indole-5-carbonitrile. pH of the reaction solution was less than 1. 1.10 g of 6,11-dihydro-5H-diindolo [2,3-a:2',3'-c] carbazole-4,7,12-tricarbonitrile (indole-7-carbonitrile trimer) with a dark blue color was obtained (yield: 77%). The resultant trimer was pressure-molded with a tablet molding machine and the mold was cut into a piece with the diameter of 10 mm and thickness of 1 mm. A conductivity thereof was measured by the four terminal method and found to be 0.70 S/cm. The result of elemental analysis was: $<C_{9.00}H_{4.00}N_{1.99}Cl_{0.11}>_3$.

Example 24

Polymerization was performed in the same way as that employed in Example 2 except that indole-4-calboxylic acid was used in place of indole-5-carbonitrile. pH of the reaction solution was less than 1. 1.20 g of 6,11-dihydro-5H-diindolo [2,3-a:2',3'-c] carbazole-1,10,15-tricarboxylic acid (indole-4-carboxylic acid trimer) was obtained (yield: 85%). The resultant trimer was pressure-molded with a tablet molding machine and the mold was cut into a piece with the diameter of 10 mm and thickness of 1 mm. A conductivity thereof was measured by the four terminal method and found to be 0.72 S/cm. The result of elemental analysis was: $<C_{9.00}H_{4.98}N_{1.00}O_{1.98}Cl_{0.13}>_3$.

Example 25

Polymerization was performed in the same way as that employed in Example 2 except that indole-6-calboxylic acid was used in place of the indole-5-carbonitrile. pH of the reaction solution was less than 1. 1.19 g of 6,11-dihydro-5H-diindolo [2,3-a:2',3'-c] calbazole-3,8,13-tricarboxylic acid (indole-6-carboxylic acid trimer) with a dark blue color was thus-obtained (yield: 84%). The resultant trimer was pressure-molded with a tablet molding machine and the mold was cut into a piece with the diameter of 10 mm and thickness of 1 mm. A conductivity thereof was measured by the four terminal method and found to be 0.77 S/cm. The result of elemental analysis was: $<C_{9.00}H_{4.99}N_{1.01}O_{1.98}Cl_{0.14}>_3$.

Example 26

Polymerization was performed in the same way as that employed in Example 2 except that indole-7-carboxylic acid was used in place of indole-5-carbonitrile. pH of the reaction solution was less than 1. 1.15 g of 6,11-dihydro-5H-diindolo [2,3-a:2',3'-c] carbazole-4,7,12-tricarboxylic acid (indole-7-carboxylic acid trimer) with a dark blue color was thus-obtained (yield: 81%). The resultant trimer was pressure-molded with a tablet molding machine and the mold was cut into a piece with the diameter of 10 mm and thickness of 1 mm. A conductivity thereof was measured by the four terminal method and found to be 0.75 S/cm. The result of elemental analysis was: $<C_{9.00}H_{4.97}N_{1.00}O_{1.98}Cl_{0.13}>_3$.

Example 27

Polymerization was performed in the same way as that employed in Example 11 except that indole-4-carbardehyde was used in place of 5-fluoroindole. pH of the reaction solution was less than 1. 1.08 g of 6,11-dihydro-5H-diindolo [2,3-a:2',3'-c] carbazole-1,10,15-tricarbardehyde (indole-4 carbaldehyde trimer) with a light green color was thus-obtained (yield: 80%). The resultant trimer was pressure-molded with a tablet molding machine and the mold was cut into a piece with the diameter of 10 mm and thickness of 1 mm. A conductivity thereof was measured by the four terminal method and found to be 0.75 S/cm. The result of elemental analysis was: $<C_{9.00}H_{4.97}N_{1.00}O_{0.99}Cl_{0.15}>_3$.

Example 28

Polymerization was performed in the same way as that employed in Example 11 except that indole-5-carbaldehyde was used in place of 5-fluoroindole. pH of the reaction solution was less than 1. 1.18 g of 6,11-dihydro-5H-diindolo [2,3-a:2',3'-c] carbazole-2,9,14-tricarbaldehyde (indole-5-carbaldehyde trimer) with a light green color was thus-obtained (yield: 87%). The resultant trimer was pressure-molded with a tablet molding machine and the mold was cut into a piece with the diameter of 10 mm and thickness of 1 mm. A conductivity thereof was measured by the four terminal method and found to be 0.82 S/cm. The result of elemental analysis was: $<C_{9.00}H_{4.99}N_{1.03}O_{1.01}Cl_{0.15}>_3$.

Example 29

Polymerization was performed in the same way as that employed in Example 11 except that indole-6-carbaldehyde was used in place of 5-fluoroindole. pH of the reaction solution was les than 1. 1.10 g of 6,11-dihydro-5H-diindolo [2,3-a:2',3'-c] carbazole-3,8,13-tricalbardehyde (indole-6-carbaldehyde trimer) with a light green color was obtained (yield: 81%). The resultant trimer was pressure-molded with a tablet molding machine and the mold was cut into a piece with the diameter of 10 mm and thickness of 1 mm. A conductivity thereof was measured by the four terminal method and found to be 0.80 S/cm. The result of elemental analysis was: $<C_{9.00}H_{4.99}N_{1.02}O_{1.01}Cl_{0.11}>_3$.

Example 30

Polymerization was performed in the same way as that employed in Example 6 except that 4-bromoindole was used in place of 5-fluoroindole. pH of the reaction solution was less than 1. 1.20 g of 1,10,15-tribromo-6,11-dihydro-5H-diindolo [2,3-a:2', 3'-c] carbazole (4-bromoindole trimer) with a light green color was thus-obtained (yield: 74%). The resultant trimer was pressure-molded with a tablet molding machine and the mold was cut into a piece with the diameter of 10 mm and thickness of 1 mm. A conductivity thereof was measured by the four terminal method and found to be 0.71 S/cm. The result of elemental analysis was: $<C_{8.00}H_{3.97}N_{1.01}Br_{0.98}Cl_{0.10}>_3$.

Example 31

Polymerization was performed in the same way as that employed in Example 6 except that 6-bromoindole was used in place of 5-fluoroindole. pH of the reaction solution was less than 1. 1.28 g of 3,8,13-tribromo-6,11-dihydro-5H-diindolo [2,3-a:2',3'-c] carbazole (6-bromoindole trimer) with a light green color was thus-obtained (yield: 79%). The resultant trimer was pressure-molded with a tablet molding machine and the mold was cut into a piece with the diameter of 10 mm and thickness of 1 mm. A conductivity thereof was measured by the four terminal method and found to be 0.73 S/cm. The result of elemental analysis was: $<C_{8.00}H_{4.01}N_{1.01}Br_{0.99}Cl_{0.12}>_3$.

Example 32

Polymerization was performed in the same way as that employed in Example 6 except that 7-bromoindole was used in place of 5-fluoroindole. pH of the reaction solution was less than 1. 1.32 g of 4,7,12-tribromo-6,11-dihydro-5H-diindolo [2,3-a:2',3'-c] carbazole (7-bromoindole trimer) with a light green color was thus-obtained (yield: 81%). The resultant trimer was pressure-molded with a tablet molding machine and the mold was cut into a piece with the diameter of 10 mm and thickness of 1 mm. A conductivity thereof was measured by the four terminal method and found to be 0.74 S/cm. The result of elemental analysis was: $<C_{8.00}H_{3.99}N_{1.02}Br_{0.99}Cl_{0.14}>_3$.

Example 33

Polymerization was performed in the same method as that employed in Example 6 except that 4-fluoroindole was used in place of 5-fluoroindole. pH of the reaction solution was less than 1. 1.32 g of 1,10,15-trifluoro-6,11-dihydro-5H-diindolo [2,3-a:2',3'-c] carbazole (4-fluoroindole trimer) with a light green color was thus-obtained (yield: 81%). The resultant trimer was pressure-molded with a tablet molding machine and the mold was cut into a piece with the diameter of 10 mm and thickness of 1 mm. A conductivity thereof was measured by the four terminal method and found to be 0.79 S/cm. The result of elemental analysis was: $<C_{8.00}H_{3.99}N_{1.02}F_{0.99}Cl_{0.12}>_3$.

Example 34

Polymerization was performed in the same way as that employed in Example 6 except that 7-fluoroindole was used in place of 5-fluoroindole. 1.35 g of 4,7,12-trifluro-6,11-dihydro-5H-diindolo [2,3-a:2',3'-c] calbazole (7-fluoroindole trimer) with a light green color was thus-obtained (yield: 83%). The resultant trimer was pressure-molded with a tablet molding machine and the mold was cut into a piece with the diameter of 10 mm and thickness of 1 mm. A conductivity thereof was measured by the four terminal method and found to be 0.81 S/cm. The result of elemental analysis was: $<C_{8.00}H_{4.01}N_{1.01}F_{0.99}Cl_{0.14}>_3$.

Example 35

Polymerization was performed in the same way as that employed in Example 16 except that 4-acetylindole was used in place of 6-acetyl indole. pH of the reaction solution was less than 1. 1.30 g of 1,10,15-triacetyl-6,11-dihydro-5H-diindolo [2,3-a:2',3'-c] carbazole (4-acetylindole trimer) with a blue-green color was thus-obtained (yield: 82%). The resultant trimer was pressure-molded with a tablet molding machine and the mold was cut into a piece with the diameter of 10 mm and thickness of 1 mm. A conductivity thereof was measured by the four terminal method and found to be 0.80 S/cm. The result of elemental analysis was: $<C_{10.00}H_{6.99}N_{0.99}O_{0.97}Cl_{0.12}>_3$.

Example 36

Polymerization was performed in the same way as that employed in Example 16 except that 7-acetylindole was used in place of 6-acetylindole. pH of the reaction solution was less than 1. 1.33 g of 4,7,12-triacetyl-6,11-dihydro-5H-diindolo [2,3-a:2',3'-c] carbazole (7-acetylindole trimer) with a blue-green color was thus-obtained (yield: 84%). The resultant trimer was pressure-molded with a tablet molding machine and the mold was cut into a piece with the diameter of 10 mm and thickness of 1 mm. A conductivity thereof was measured by the four terminal method and found to be 0.82 S/cm. The result of elemental analysis was: $<C_{10.00}H_{7.01}N_{0.99}O_{0.99}Cl_{0.13}>_3$.

Example 37

Polymerization was performed in the same way as that employed in Example 2 except that 4-carbamoyl indole was used in place of indole-5-carbonitrile. pH of the reaction solution was less than 1. 1.10 g of 1,10,15-triamide-6,11-dihydro-5H-diindolo [2,3-a:2',3'-c] carbazole (4-carbamoyl indole trimer) with a dark blue color was thus-obtained (yield: 77%). The resultant trimer was pressure-molded with a tablet molding machine and the mold was cut into a piece with the diameter of 10 mm and thickness of 1 mm. A conductivity thereof was measured by the four terminal method and found to be 0.85 S/cm. The result of elemental analysis was: $<C_{9.00}H_{6.00}N_{2.02}O_{0.97}Cl_{0.14}>_3$.

Example 38

Polymerization was performed in the same way as that employed in Example 2 except that 5-carbamoyl was used in place of indole-5-carbonitrile. pH of the reaction solution was less than 1. 1.23 g of 2,9,14-triamide-6,11-dihydro-5H-diindolo [2,3-a:2',3'-c] carbazole (5-carbamoyl indole trimer) with a dark blue color was thus-obtained (yield: 87%). The resultant trimer was pressure-molded with a tablet molding machine and the mold was cut into a piece with the diameter of 10 mm and thickness of 1 mm. A conductivity thereof was measured by the four terminal method and found to be 0.95 S/cm. The result of elemental analysis was: $<C_{9.00}H_{5.99}N_{2.02}O_{0.98}Cl_{0.15}>_3$.

Example 39

Polymerization was performed in the same way as that employed in Example 11 except that 6-carbamoyl indole was used in place of 5-fluoroindole. pH of the reaction solution was less than 1. 1.12 g of 3,8,13-triamide-6,11-dihydro-5H-diindolo [2,3-a:2',3'-c] carbazole (6-carbamoyl indole trimer) with a dark blue color was thus-obtained (yield: 83%). The resultant trimer was pressure-molded with a tablet molding machine and the mold was cut into a piece with the diameter of 10 mm and thickness of 1 mm. A conductivity thereof was measured by the four terminal method and found to be 0.79 S/cm. The result of elemental analysis was: $<C_{9.00}H_{5.98}N_{2.00}O_{0.99}Cl_{0.12}>_3$.

Example 40

Polymerization was performed in the same way as that employed in Example 11 except that 7-carbamoyl indole was used in place of 5-fluoroindole. pH of the reaction solution was less than 1. 1.07 g of 4,7,12-triamide-6,11-dihydro-5H-diindolo [2,3-a:2',3'-c] carbazole (7-carbamoyl indole trimer) with a dark blue color was thus-obtained (yield: 79%). The resultant trimer was pressure-molded with a tablet molding machine and the mold was cut into a piece with the diameter of 10 mm and thickness of 1 mm. A conductivity thereof was measured by the four terminal method and found to be 0.80 S/cm. The result of elemental analysis was: $<C_{9.00}H_{6.01}N_{1.99}O_{0.99}Cl_{0.13}>_3$.

Comparative Example

The three representative indole derivative trimers among those described above were compared to polyaniline (J. Polymer Sci., Plymer Chem. Ed., 26, 1531 (1988)) as well as to polydithiodianiline (JP-A-10-265567) by means of the electrochemical measurement (cyclic voltammetry). More specifically, 500 mg of each of the three indole derivative trimers, polyaniline, and polydithiodianiline was suspended in 100 ml of 1M-NaOH aqueous solution for 2 hours at the temperature of 20° C., then separated with a perforated funnel, washed with water and dried. Each of them was then dissolved in 20 ml of dimethylformamide, which was applied on a platinum electrode (with the surface area of 5 mm×5 mm), and baked at the temperature of 100° C. to prepare a thin film electrode of each of the indole derivative trimers, polyaniline, and polydithiodianiline, respectively. Measurement cells consisting of each of the thin film electrodes obtained as described above as a working electrode, a platinum electrode as a counter electrode, and a KCl saturated calomel electrode (SCE) as a reference electrode, and a LiClO₄ aqueous solution (0.2 M) as the electrolyte, were prepared. The cycle test was performed for each of the thin film electrodes under the voltage in the range from −0.3 to 1.2 V (against the SCE), and the obtained cyclic voltamgram and recorded oxidation-reduction potential $E_o$ and the total reduction capacity were measured.

Comparative data of the oxidation-reduction potential $E_o$, the total reduction capacity, and cyclic characteristic for the five types of trimers are shown in Table 1.

TABLE 1

| Sample | Oxidation-Reduction Potential $E_o$(V) | Total Reduction Capacity (C/g) | Cycle Characteristic (%) |
|---|---|---|---|
| Example 2 | 1.00 | 330 | 85 |
| Example 3 | 1.10 | 320 | 97 |
| Example 4 | 0.95 | 350 | 93 |
| Example 9 | 0.98 | 335 | 93 |
| Example 12 | 1.05 | 315 | 88 |
| Example 13 | 0.95 | 298 | 90 |
| Polyaniline | 0.52 | 235 | 38 |
| Polydithiodianiline | 0.60 | 260 | 50 |

The cycle characteristic as used herein indicates a percentage of the reduction capacity at the 10000-th cycle, assuming that the reduction capacity at the first cycle is 100.

Comparison of Strength

Each of the indole derivative trimers described in Examples 2, 4, and 12 was pulverized by a blender (Model HGB-SS produced by WARING COMMERCIAL CORP.) at a rotational speed of 11,000 rpm for 3 minutes respectively. Comparative data on particle diameter distribution of the trimers before and after the pulverization and the mechanical strength of pellets for IR measurement thereof are as shown in Table 2.

TABLE 2

|  | Pulverizing process | Diameter distribution (μm) | Mechanical strength |
|---|---|---|---|
| Example 2 | No | 4.0~450 | Δ |
|  | Yes | 3.0~40 | ⊚ |
| Example 4 | No | 20~800 | Δ |
|  | Yes | 0.15~25 | ○ |
| Example 12 | No | 5.0~750 | Δ |
|  | Yes | 0.20~50 | ○ |

⊚: Very strong
○: Strong
Δ: Relatively weak

INDUSTRIAL APPLICABILITY

As described above, with the present invention, it was possible to provide a method of producing conductive indole derivative trimers with the excellent oxidation-reduction capacity and also with the excellent cycle characteristic in an industrial scale. The chemical oxidization method according to the present invention enables mass production of a large quantity of the indole derivative trimers, so that the method is very suitable for industrial production. On the other hand, with the conventional electrolytic oxidation, the mass production could hardly be achieved because of peculiarity of the apparatus used therein. Unlike the electrolytic reaction, the final cyclization reaction in the chemical reaction is an oxidative cyclization reaction by Lewis acid under mild conditions, and therefore trimers with excellent conductivity containing little impurities can be obtained without excessively oxidizing the trimers themselves. Among the indole derivative trimers obtained by the method of the present invention, 4-nitroindole derivative trimer, 6-nitroindole derivative trimer, 7-nitroindole derivative trimer, indole-4-carbonitrile derivative trimer, indole-6-carbonitrile derivative trimer, indole-7-carbonitrile derivative trimer, indole-4-carboxylic acid derivative trimer, indole-6-carboxylic acid derivative trimer, indole-7-carboxylic acid derivative trimer, indole-4-carbaldehyde derivative trimer, indole-5-carbardehyde derivative trimer, indole-6-carbardehyde derivative trimer, indole-7-carbardehhyde derivative trimer, 4-bormoindole derivative trimer, 6-bormoindole derivative trimer, 7-bromoindole derivative trimer, 4-fluoroindole derivative trimer, 5-fluoroindole derivative trimer, 6-fluoroindole derivative trimer, 7-fluroindole derivative trimer, 4-carbamoylindole derivative trimer, 5-carbamoyl derivative trimer, 6-carbamoylindole derivative trimer, 7-carbamoylindole derivative trimer, 4-acetylindole derivative trimer, 5-acetylindole derivative trimer, 6-acetylindole derivative trimer, and 7-acetylindole derivative trimer are more excellent in their conductivity, oxidation-reduction potential and/or oxidation-reduction capacity, and cyclic characteristic, as compared to the known indole derivative trimers. These indole derivative trimers can be used for preventing electrifications, electrostatic shielding, capacitors, batteries, EMI shielding, chemical sensors, display devices, non-linear materials, anti-rust agents, adhesives, textiles, antistatic paints, primers for plating, underground for electrostatic plating, and electrolytic protection and the like.

The invention claimed is:

1. An indole derivative trimer of following formula (3):

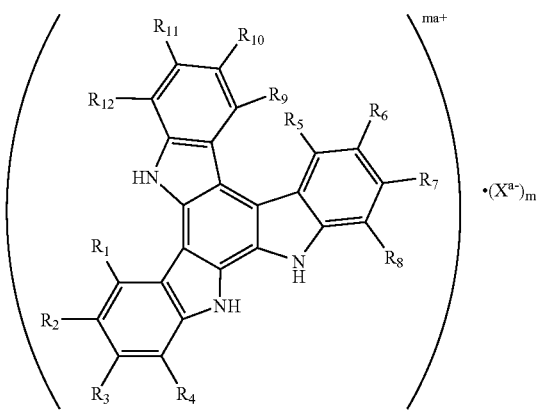

(3)

wherein $R_1$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group, providing that the cases where all of $R_1$ to $R_{12}$ are hydrogen and where all of $R_2$, $R_6$ and $R_{10}$ are substituted by the same substituent and the rest of the substituents are all hydrogen are excluded;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 indicating the ionic valence of the ion X; and m is a number in the range from 0.001 to 0.5.

2. A 4-nitroindole trimer derivative of following formula (4):

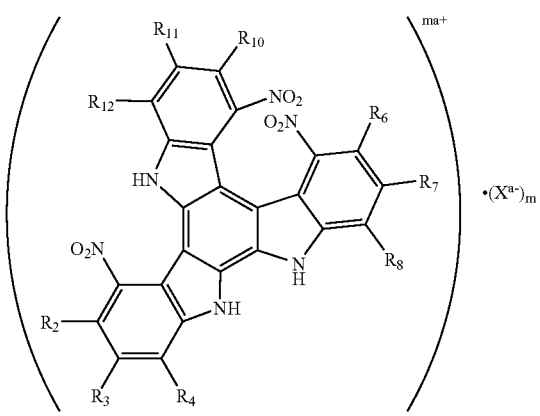

(4)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoromethane sulfonate ion;

a is an integral number in the range from 1 to 3 representing the ionic valence of the ion X; and m is a number in the range from 0.001 to 0.5.

3. A 6-nitroindole trimer derivative of following formula (5):

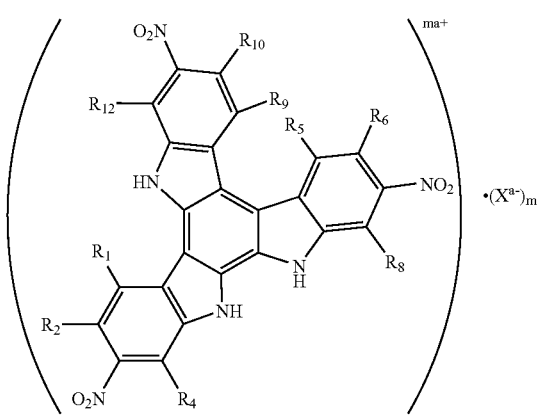

(5)

wherein $R_1$, $R_2$, $R_4$ to $R_6$, and $R_8$ to $R_{10}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

4. A 7-nitroindole trimer derivative of following formula (6):

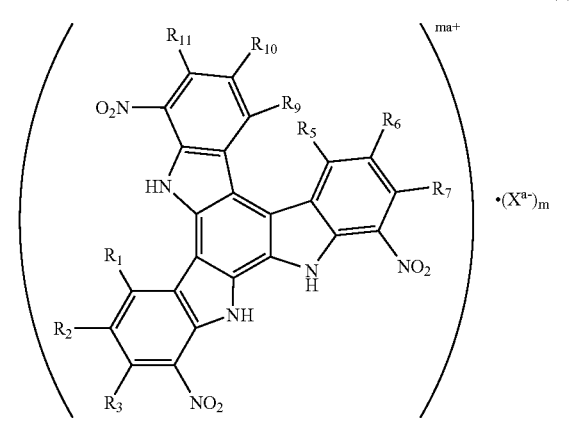

(6)

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

5. An indole-4-carbonitrile trimer derivative of following formula (7):

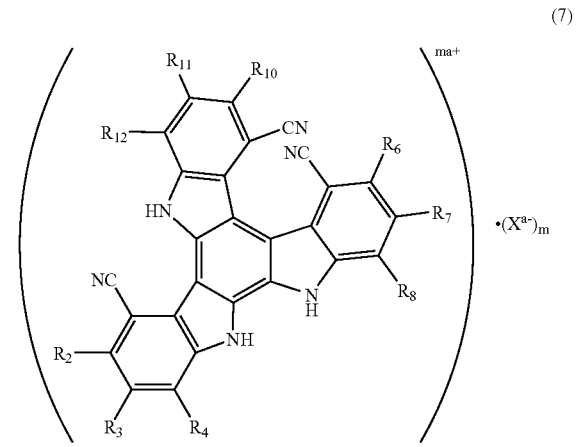

(7)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

6. An indole-6-carbonitrile trimer derivative of following formula (8):

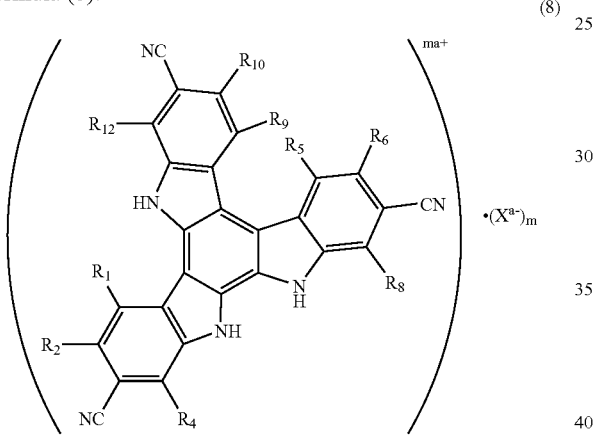

(8)

wherein $R_1$, $R_2$, $R_4$ to $R_6$, $R_8$ to $R_{10}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

7. An indole-7-carbonitrile trimer derivative of following formula (9):

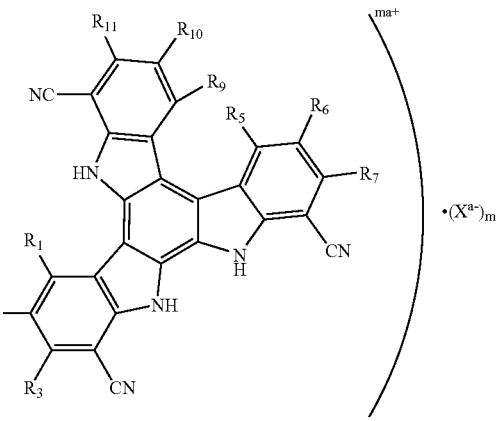

(9)

wherein $R_1$ to $R_3$, $R_5$ to $R_7$, and $R_9$ to $R_{11}$, are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

8. An indole-4-carboxylic acid trimer derivate of formula (10),

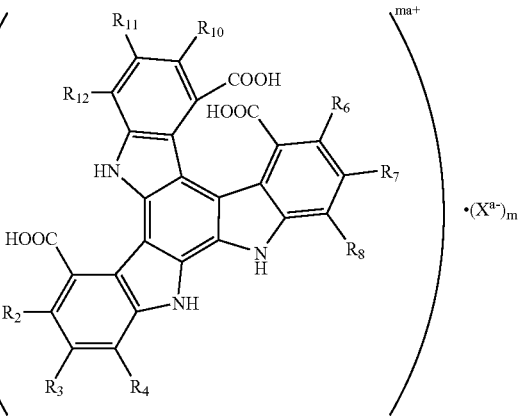

(10)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

9. An indole-6-carboxylic acid trimer derivative expressed by the following formula (11):

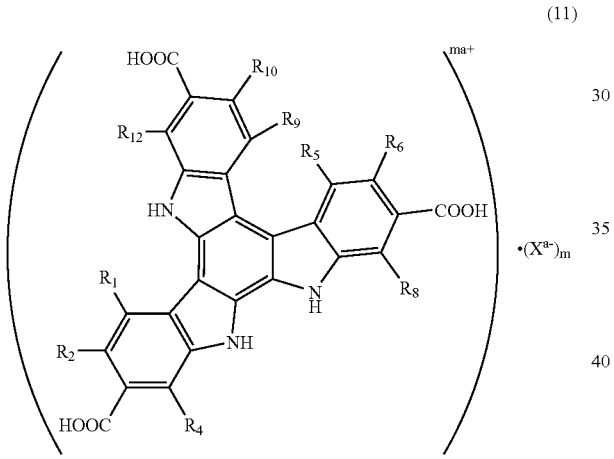

(11)

wherein $R_1$, $R_2$, $R_4$ to $R_6$, $R_8$ to $R_{10}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

10. An indole-7-carboxylic acid trimer derivative of formula (12):

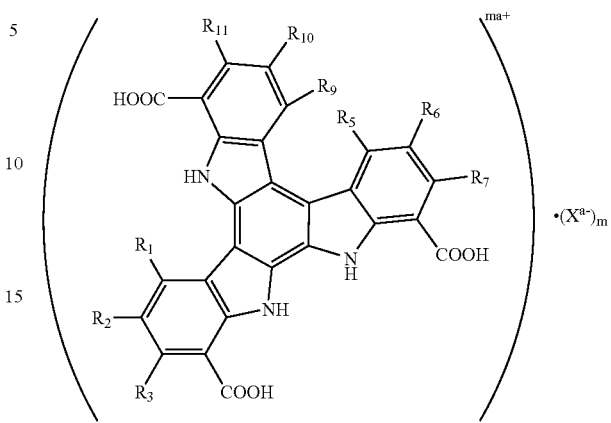

(12)

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

11. An indole-4-carbaldehyde trimer derivate of following formula (13):

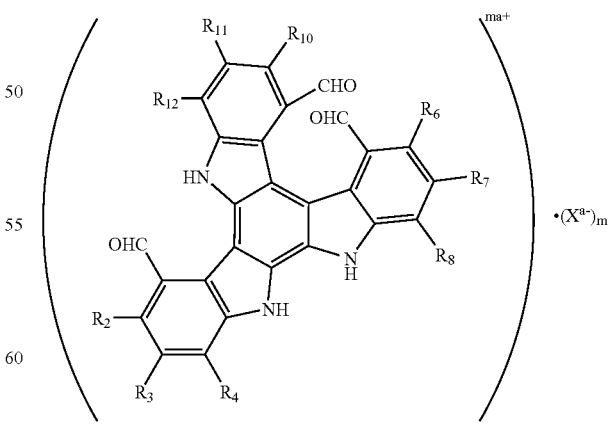

(13)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

12. An indole-5-carbaldehyde trimer derivative of following formula (14):

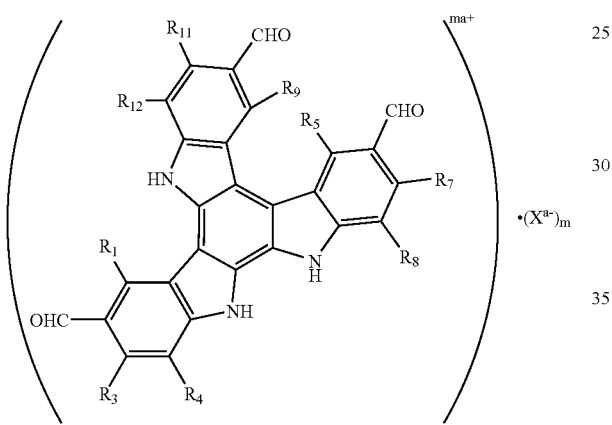

(14)

wherein $R_1$, $R_3$ to $R_5$, $R_7$ to $R_9$, $R_{11}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

13. An indole-6-carbaldehyde trimer derivative of formula (15):

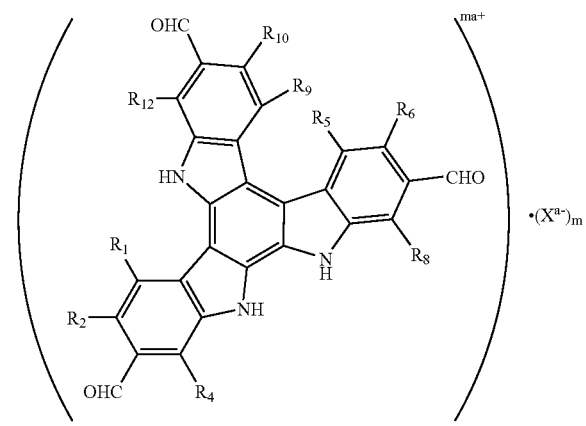

(15)

wherein $R_1$, $R_2$, $R_4$ to $R_6$, $R_8$, to $R_{10}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

14. An indole-7-carbaldehyde trimer derivative of following formula (16):

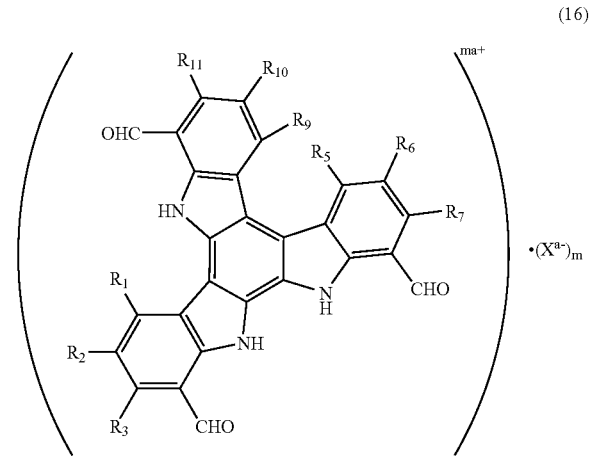

(16)

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

15. A 4-bromoindole trimer derivative of formula (17):

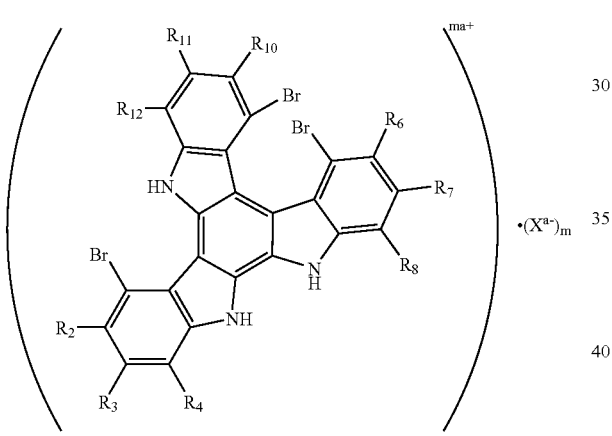

(17)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

16. A 6-bromoindole trimer derivative of following formula (18):

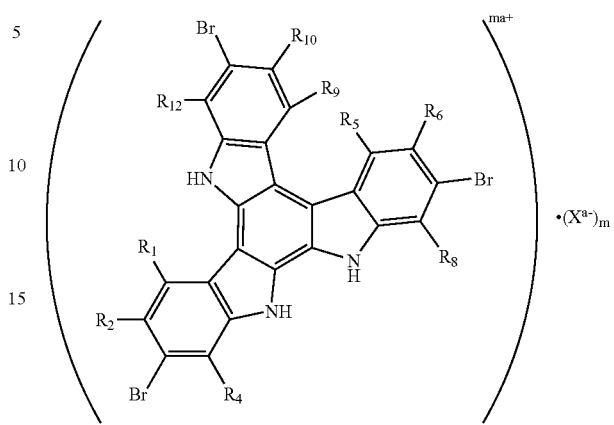

(18)

wherein $R_1$, $R_2$, $R_4$ to $R_6$, $R_8$ to $R_{10}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

17. A 7-bromoindole trimer derivative of following formula (19):

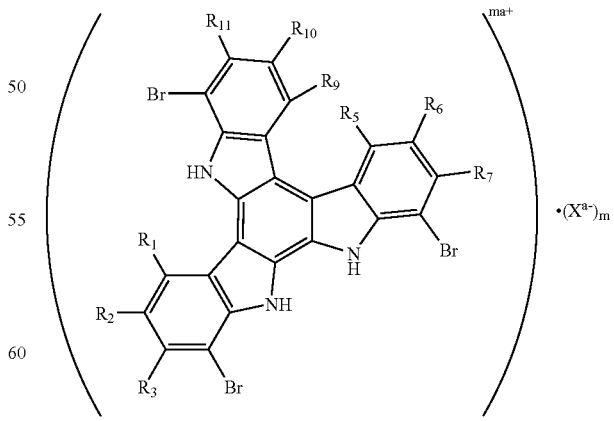

(19)

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

18. A 4-fluoroindole trimer derivative of following formula (20):

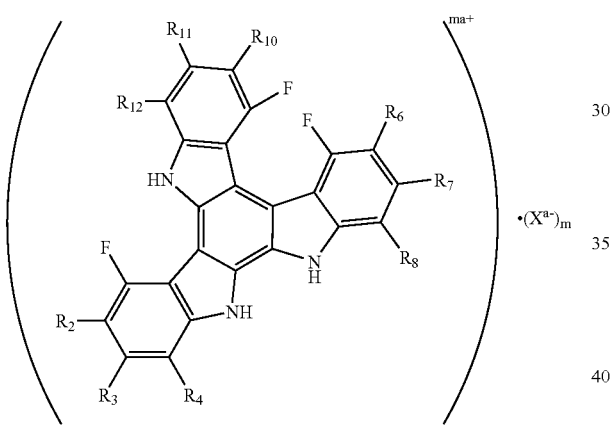

(20)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

19. A 5-fluoroindole trimer derivative of formula (21):

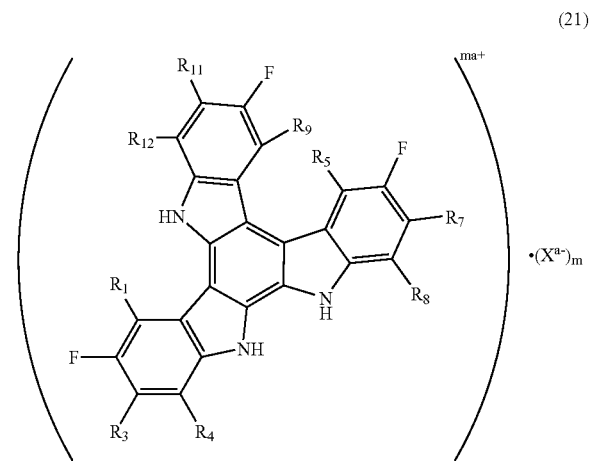

(21)

wherein $R_1$, $R_3$ to $R_5$, $R_7$ to $R_9$, $R_{11}$ and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

20. A 6-fluoroindole trimer derivative of formula (22):

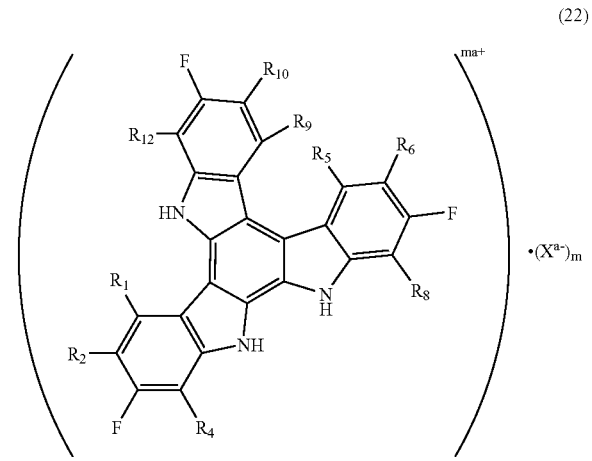

(22)

wherein $R_1$, $R_2$, $R_4$ to $R_6$, $R_8$ to $R_{10}$ and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

21. A 7-fluoroindole trimer derivative of formula (23):

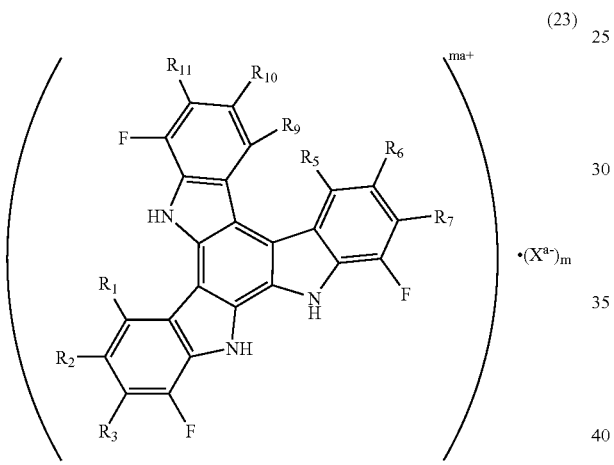

(23)

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

22. A 4-acetylindole trimer derivative of following formula (24):

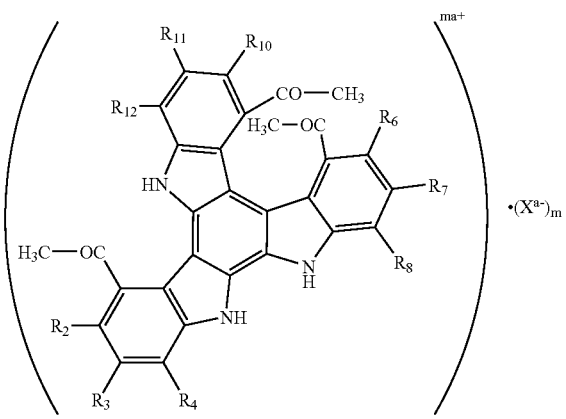

(24)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

23. A 5-acetylindole trimer derivative of following formula (25):

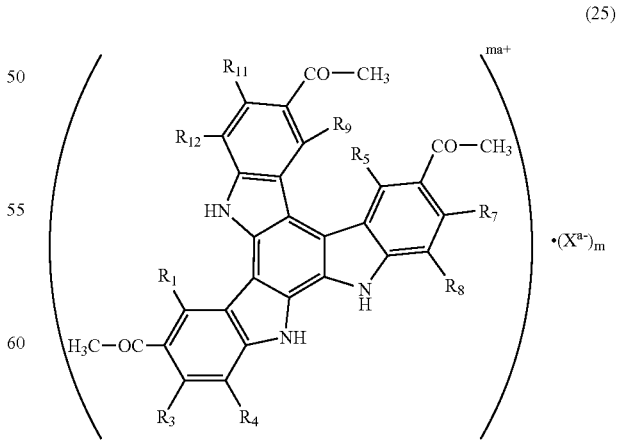

(25)

wherein $R_1$, $R_3$ to $R_5$, $R_7$ to $R_9$, $R_{11}$ and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

24. A 6-acetylindole trimer derivative of following formula (26):

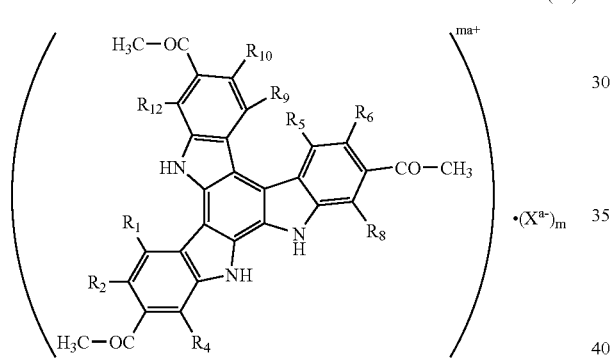

(26)

wherein $R_1$, $R_2$, $R_4$ to $R_6$, $R_8$ to $R_{10}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

25. A 7-acetylindole trimer derivative of following formula (27):

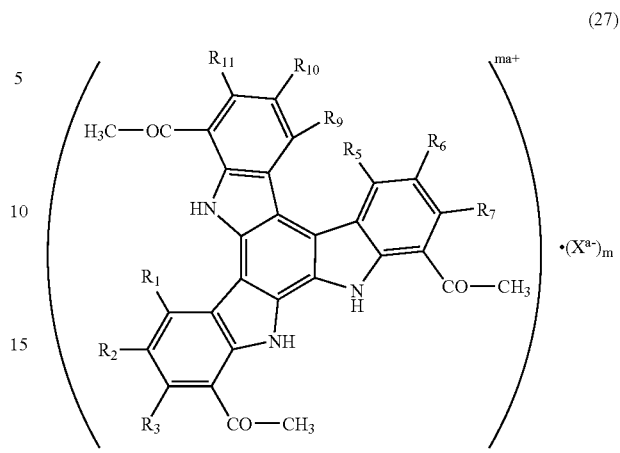

(27)

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

26. A 4-carbamoylindole trimer derivative of following formula (28):

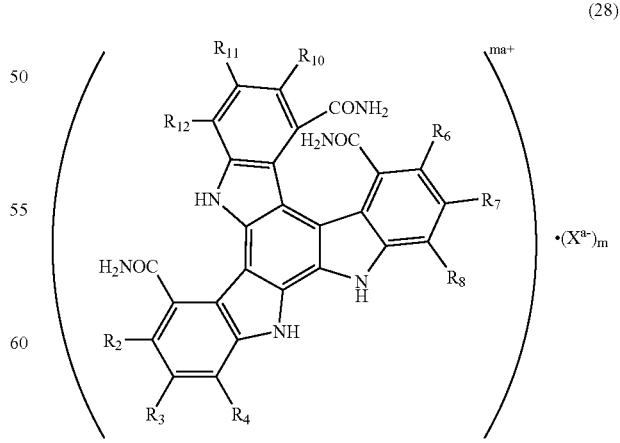

(28)

wherein $R_2$ to $R_4$, $R_6$ to $R_8$, and $R_{10}$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

27. A 5-carbamoylindole trimer derivative of following formula (29):

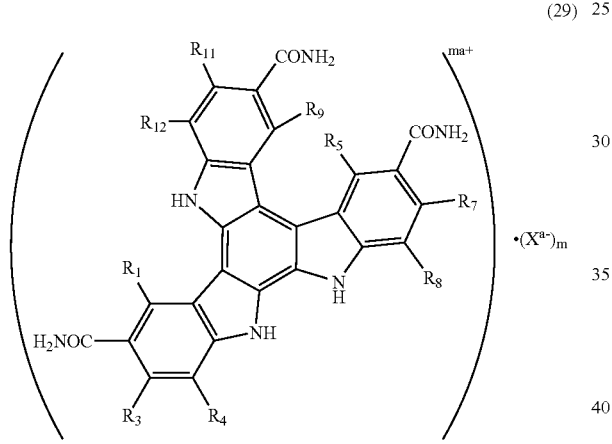

(29)

wherein $R_1$, $R_3$ to $R_5$, $R_7$ to $R_9$, $R_{11}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

28. A 6-carbamoylindole trimer derivative of following formula (30):

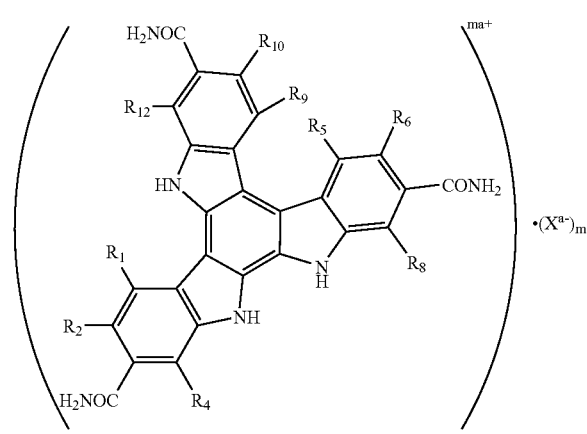

(30)

wherein $R_1$, $R_2$, $R_4$ to $R_6$, $R_8$ to $R_{10}$, and $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

29. A 7-carbamoylindole trimer derivative of following formula (31):

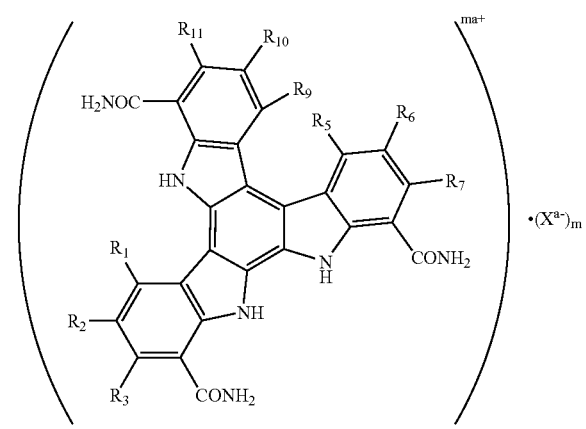

(31)

wherein $R_1$ to $R_3$, $R_5$ to $R_7$, and $R_9$ to $R_{11}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

30. The indole derivative trimer according to claim 1, wherein $X^{a-}$ is at least one member selected from the group consisting of chlorine ion, sulfate ion, and fluoroborate ion.

31. The indole derivative trimer according to claim 1, the indole derivative trimer is of doped type with m=0.001-0.5.

32. The indole derivative trimer according to claim 1, wherein the indole derivative trimer is of undoped type with m=0.

33. An indole derivative trimer of following formula (2) in the form of particles having a particle diameter of 0.1 to 50 µm:

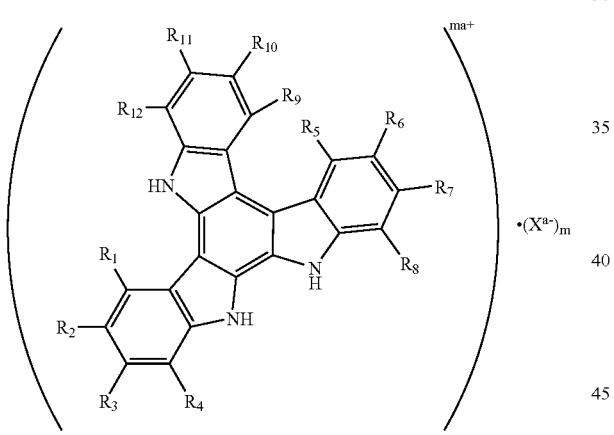

(2)

wherein $R_1$ to $R_{12}$ are substituents each independently selected from the group consisting of hydrogen, linear or branched alkyl group having 1 to 24 carbon atoms, linear or branched alkoxy group having 1 to 24 carbon atoms, linear or branched acyl group having 2 to 24 carbon atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

34. The indole derivative trimer according to claim 33, wherein the indole derivative trimer is obtained by reacting at least one indole derivative (A) of formula (1):

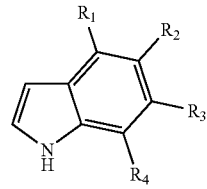

(1)

wherein $R_1$ to $R_4$ are substituents selected independently from the group consisting of hydrogen, linear or branched alkyl group having 1 to 24 carbon atoms, linear or branched alkoxy group having 1 to 24 carbon atoms, linear or branched acyl group having 2 to 24 atoms, aldehyde group, carboxyl group, linear or branched carboxylic ester group having 2 to 24 carbon atoms, sulfonic group, linear or branched sulfonic ester group having 1 to 24 carbon atoms, cyano group, hydroxyl group, nitro group, amino group, amide group, and halogen group, in a reaction mixture containing at least one oxidant (B) and at least one organic solvent (C).

35. The indole derivative trimer according to claim 33, wherein $R_1$, $R_9$, and $R_5$ are a radical of the formula $NO_2$.

36. The indole derivative trimer according to claim 33, wherein the indole derivative trimer is an indole-5-carbonitrile trimer or an indole-5-carboxylic acid trimer of following formula (32):

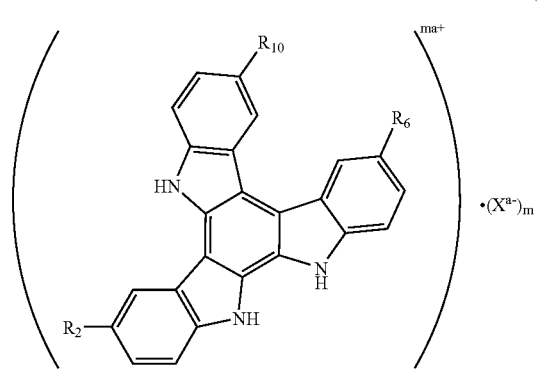

(32)

wherein $R_2$, $R_6$, and $R_{10}$ are substituted by cyano group or carboxyl group;

$X^{a-}$ is at least one anion selected from the group of monovalent to tervalent anions consisting of chlorine ion, bromine ion, iodine ion, fluorine ion, nitrate ion, sulfate ion, hydrogen sulfate ion, phosphate ion, fluoroborate ion, perchlorate ion, thiocyanate ion, acetate ion, propionate ion, methane sulfonate ion, p-toluene sulfonate ion, trifluoroacetate ion, and trifluoeomethane sulfonate ion;

a is an integral number in the range from 1 to 3 representing the ionic valence of the ion X; and m is a number in the range from 0.001 to 0.5.

* * * * *